(12) United States Patent
Yamauchi et al.

(10) Patent No.: US 9,321,600 B2
(45) Date of Patent: Apr. 26, 2016

(54) AUTOMATIC ANALYZER

(71) Applicants: Kabushiki Kaisha Toshiba, Minato-ku (JP); Toshiba Medical Systems Corporation, Otawara-shi (JP)

(72) Inventors: Shigeya Yamauchi, Nasushiobara (JP); Eiichi Azuma, Nasushiobara (JP)

(73) Assignees: KABUSHIKI KAISHA TOSHIBA, Minato-ku (JP); Toshiba Medical Systems Corporation, Otawara-shi (JP)

( * ) Notice: Subject to any disclaimer, the term of this patent is extended or adjusted under 35 U.S.C. 154(b) by 95 days.

(21) Appl. No.: 14/093,291

(22) Filed: Nov. 29, 2013

(65) Prior Publication Data
US 2014/0090957 A1 Apr. 3, 2014

Related U.S. Application Data

(63) Continuation of application No. PCT/JP2012/064206, filed on May 31, 2012.

(30) Foreign Application Priority Data

May 31, 2011 (JP) ................................. 2011-122676
May 31, 2011 (JP) ................................. 2011-122685

(51) Int. Cl.
*B65G 43/08* (2006.01)
*B65G 47/52* (2006.01)
(Continued)

(52) U.S. Cl.
CPC ................ *B65G 47/52* (2013.01); *G01N 35/04* (2013.01); *G01N 35/026* (2013.01);
(Continued)

(58) Field of Classification Search
CPC .. B65G 43/08; B65G 43/10; B65G 2203/042; B65G 2201/0261; B65H 2220/01; B65H 2220/02
USPC .......... 198/571, 572, 803.14, 803.15, 867.11, 198/867.12
See application file for complete search history.

(56) References Cited

U.S. PATENT DOCUMENTS 3,630,338 A * 12/1971 Oberli ......................... 198/464.2
3,817,368 A * 6/1974 Wentz et al. .................. 198/572
(Continued)

FOREIGN PATENT DOCUMENTS

CN 101520463 A 9/2009
CN 101558314 A 10/2009
(Continued)

OTHER PUBLICATIONS

International Search Report mailed Aug. 28, 2012 for PCT/JP2012/064206 filed on May 31, 2012 with English Translation.
(Continued)

*Primary Examiner* — James R Bidwell
(74) *Attorney, Agent, or Firm* — Oblon, McClelland, Maier & Neustadt, L.L.P

(57) ABSTRACT

A convey mechanism is a moving mechanism used to move a rack, which can store cuvettes, along a linear moving direction. A driving unit drives the convey mechanism to intermittently move the rack along. A detection unit outputs an error signal when it detects that a placement state of the rack on the convey mechanism corresponds to an error placement which does not allow the convey mechanism to normally convey the rack, and does not output any error signal when it detects that the placement state does not correspond to the error placement. A controller controls the driving unit to stop a convey operation of the rack when the error signal is output. The controller controls the driving unit to execute the convey operation of the rack when the error signal is not output.

13 Claims, 17 Drawing Sheets

(51) Int. Cl.
 *G01N 35/04* (2006.01)
 *G01N 35/02* (2006.01)

(52) U.S. Cl.
 CPC ............... *G01N 2035/0415* (2013.01); *G01N 2035/0465* (2013.01); *G01N 2035/0484* (2013.01); *G01N 2035/0494* (2013.01)

(56) References Cited

U.S. PATENT DOCUMENTS

| | | | |
|---|---|---|---|
| 6,390,281 B1 * | 5/2002 | Nagai et al. | 198/572 |
| 7,263,409 B2 * | 8/2007 | LeVasseur et al. | 700/228 |
| 2010/0181167 A1 * | 7/2010 | Tachibana | 198/572 |
| 2012/0175225 A1 * | 7/2012 | Breen et al. | 198/571 |

FOREIGN PATENT DOCUMENTS

| | | |
|---|---|---|
| JP | 55-86959 | 6/1980 |
| JP | 60-193437 U | 12/1985 |
| JP | 3-285173 A | 12/1991 |
| JP | 8-304414 A | 11/1996 |
| JP | 8-304415 A | 11/1996 |
| JP | 9-196926 A | 7/1997 |
| JP | 11-106018 A | 4/1999 |
| JP | 2001-272408 A | 10/2001 |
| JP | 2006-189362 A | 7/2006 |
| JP | 2008-541054 A | 11/2008 |
| JP | 2010-139371 A | 6/2010 |
| JP | 2010-181384 A | 8/2010 |

OTHER PUBLICATIONS

International Written Opinion mailed Aug. 28, 2012 for PCT/JP2012/064206 filed on May 31, 2012.

Office Action and Search Report issued on Dec. 26, 2013 in the corresponding Chinese Patent Application No. 201280000627.6 (with English Translation).

Office Action issued May 12, 2015 in Japanese Patent Application No. 2011-122676.

* cited by examiner

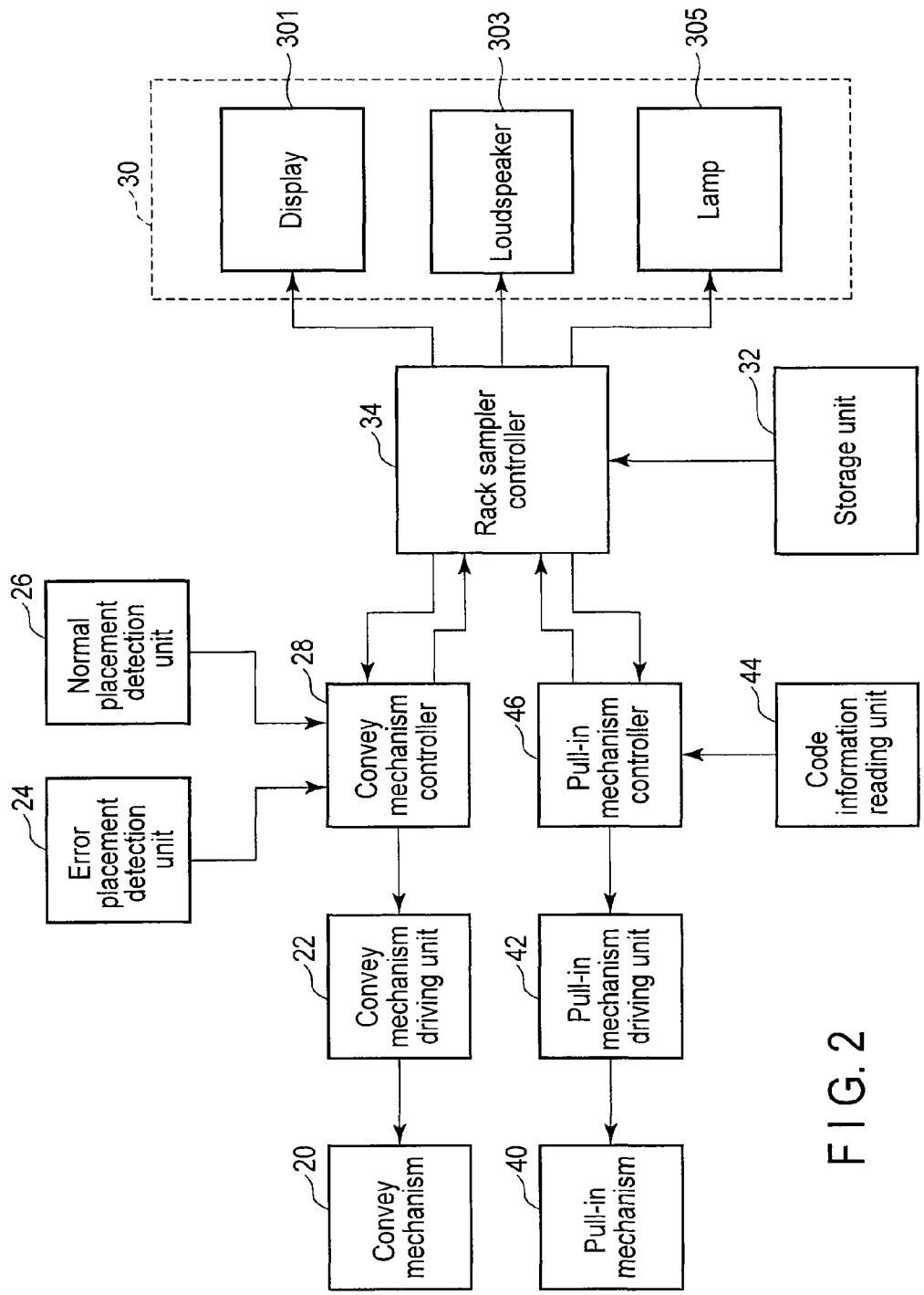
F I G. 2

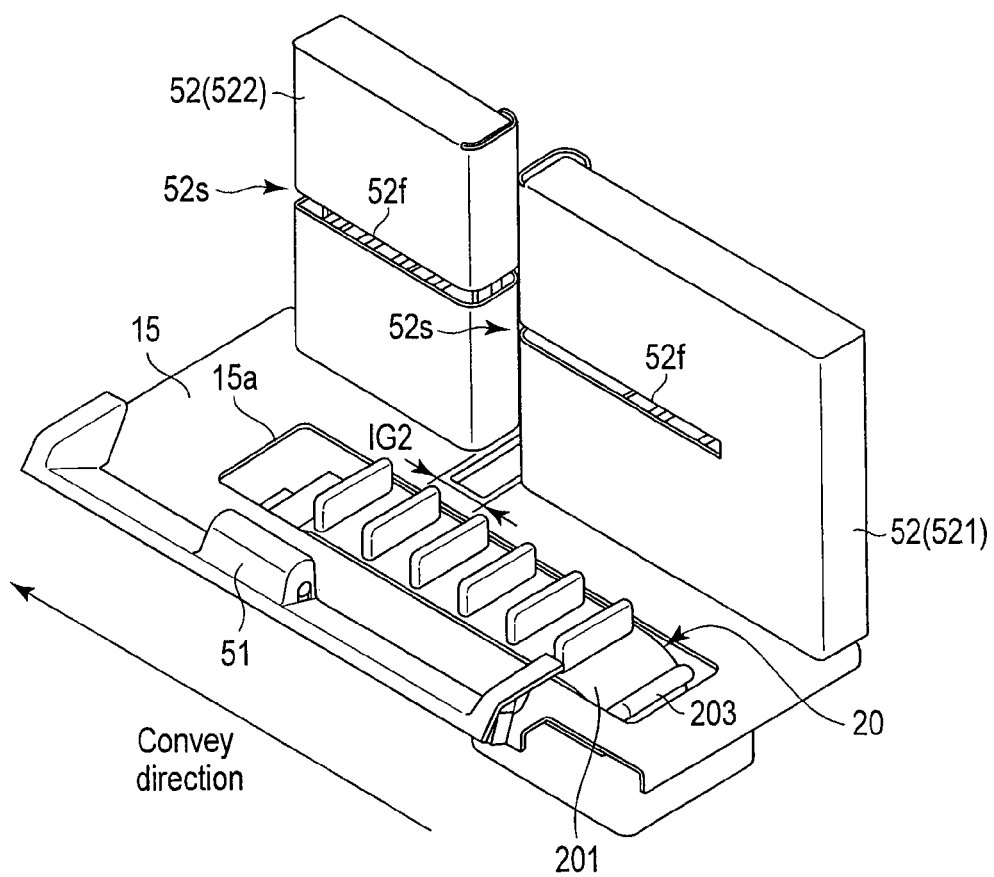
F I G. 6

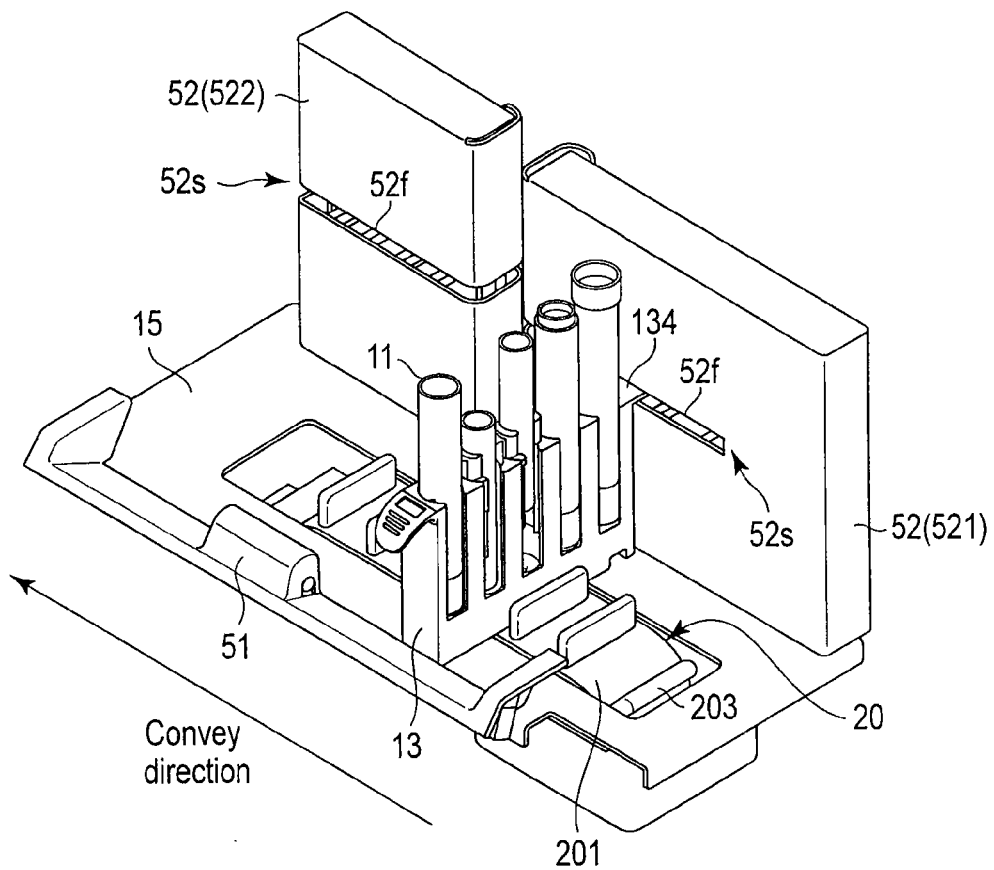
F I G. 7

Placement improper for conveyance (error placement)

Placement proper for conveyance (normal placement)

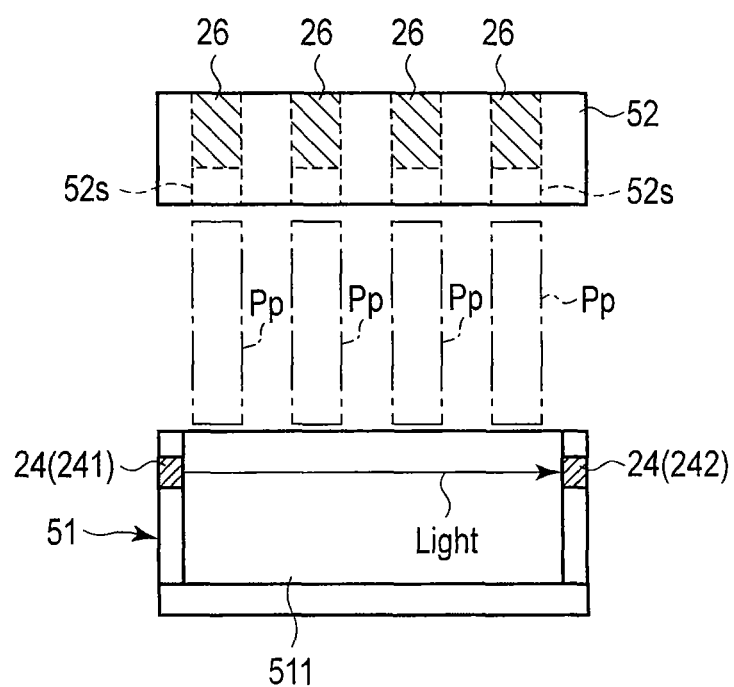
F I G. 12

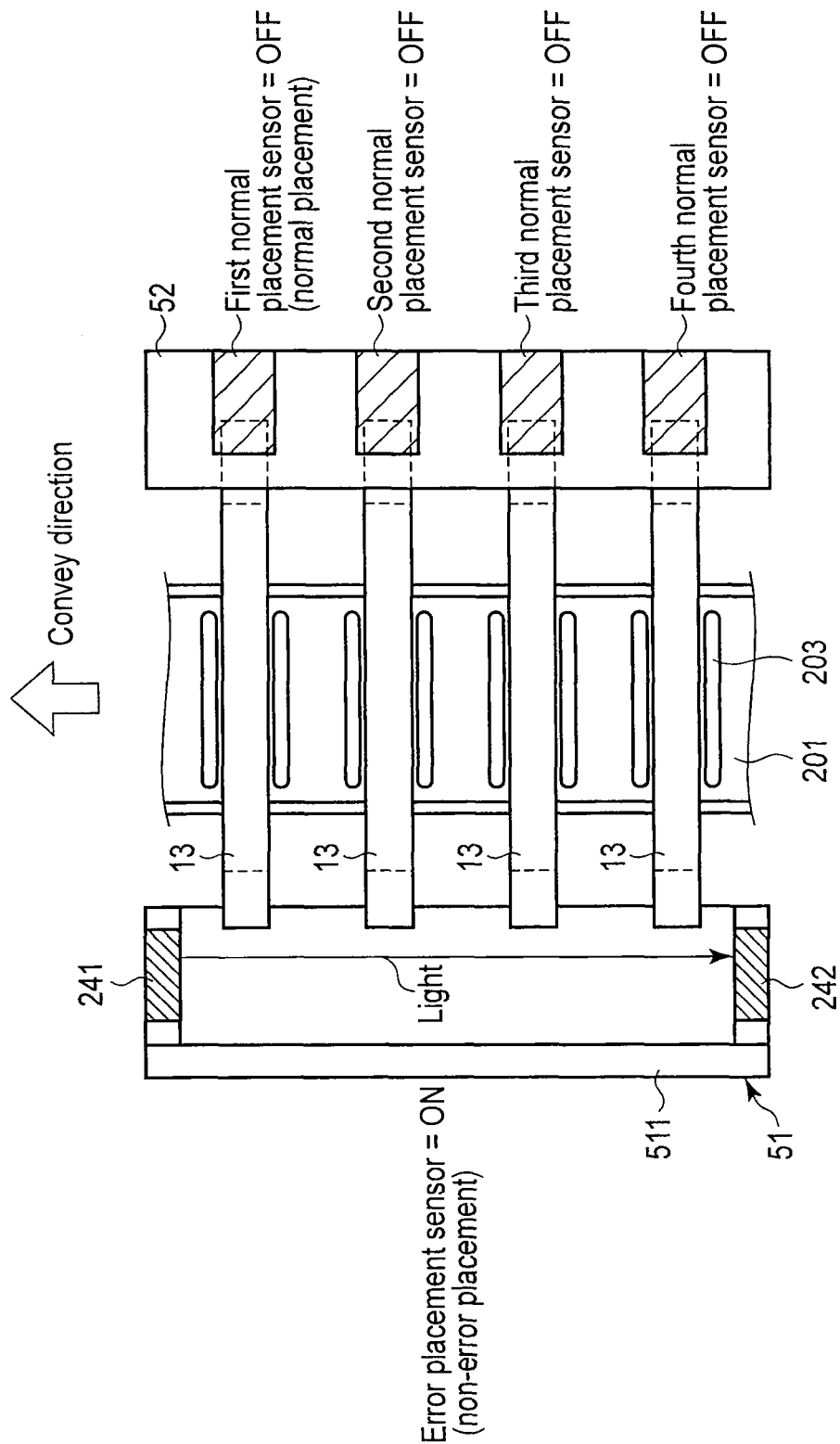
F I G. 13

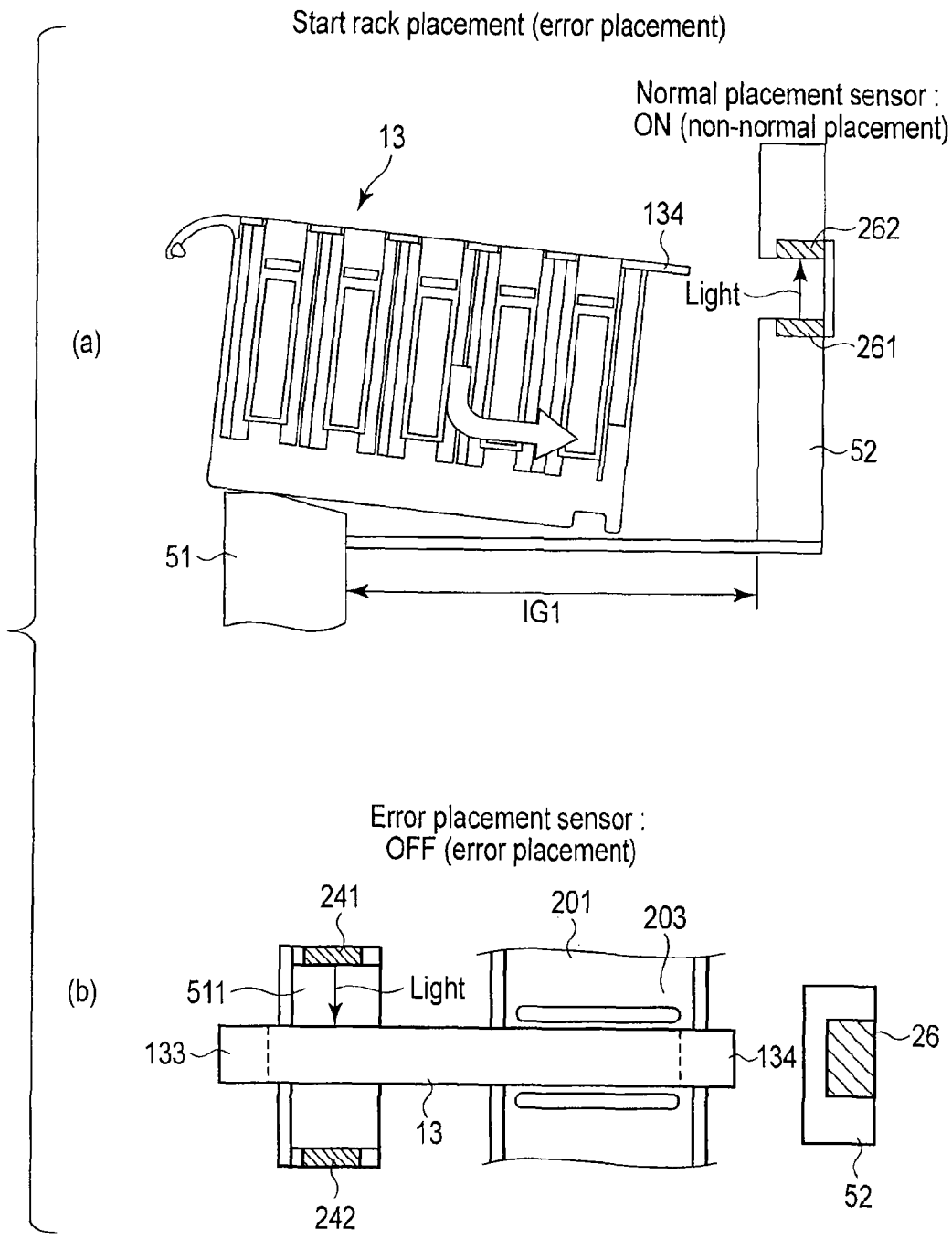
F I G. 15

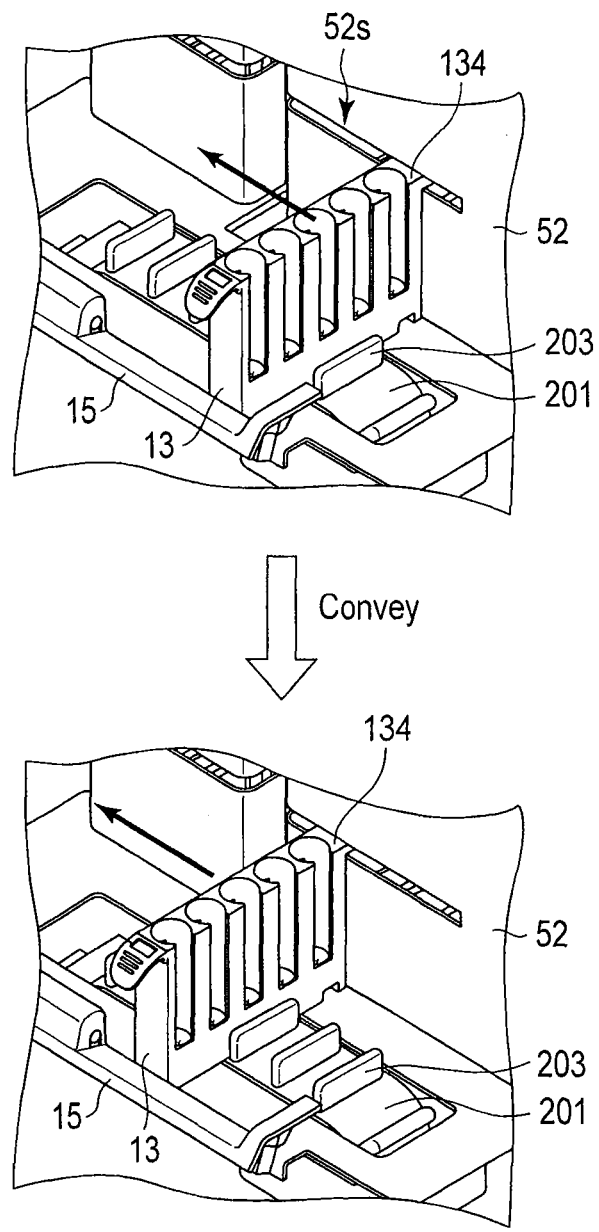
F I G. 18

AUTOMATIC ANALYZER

CROSS-REFERENCE TO RELATED APPLICATIONS

This application is a Continuation Application of PCT Application No. PCT/JP2012/064206, filed May 31, 2013 and based upon and claims the benefit of priority from the Japanese Patent Application No. 2011-122676, filed May 31, 2011, and the Japanese Patent Application No. 2011-122685, filed May 31, 2011, the entire contents of all of which are incorporated herein by reference.

FIELD

An embodiment described herein relates generally to an automatic analyzer.

BACKGROUND

An automatic analyzer of a type, which uses a rack sampler, has been developed. The automatic analyzer of this type is equipped with, for example, a convey mechanism and pull-in mechanism. The convey mechanism conveys a rack which stores cuvettes containing samples to be measured using a belt conveyor and the like to a pull-in position. The pull-in mechanism pulls in the rack from the pull-in position to a sample suction position.

When the rack is not accurately placed at a placement position on the convey mechanism, the rack may fall or the position of a cuvette of a sample to be measured may deviate from the sample suction position.

The following methods for detecting whether or not the rack is normally placed on the convey mechanism are adopted.

1. A movable portion, which moves by the self weight of the rack, is set on the convey mechanism. The movement of the movable portion is detected by a sensor. A mechanism in which the movement of the movable portion changes depending on whether or not the rack is placed at an accurate position is provided. By detecting the movement of the movable portion, whether or not the rack is placed at an accurate placement position is detected. In this case, it is difficult to balance between the self weight of the rack and a change in movement of the movable portion. Since the rack is moved by the movable portion, the rack readily falls. In order to avoid falling, the size of the rack has to be increased, thus disturbing a size reduction of the rack and apparatus.

2. A sensor for detecting the rack is set on the pull-in mechanism of the rack. This sensor is used to confirm whether or not the track is accurately pulled in and whether or not the rack is accurately placed at the pull-in position. In this manner, whether or not the rack is placed at a rack placement position of the convey mechanism can be confirmed. However, in this case, whether or not the rack is accurately placed at the rack placement position on the convey mechanism cannot be confirmed before the rack is conveyed to the pull-in position.

An object of the embodiment is to provide an automatic analyzer which can safely convey a rack after the rack is placed at an accurate position on a convey mechanism.

BRIEF DESCRIPTION OF THE DRAWING

FIG. 2 is a functional block diagram of the automatic analyzer according to this embodiment.

FIG. 6 is a perspective view of a convey mechanism portion included in the rack sampler in FIG. 1.

FIG. 7 is a perspective view of the convey mechanism portion in FIG. 6 on which the rack according to this embodiment is placed.

FIG. 12 is a plan view of the front-side guide and back-side guide included in the rack sampler in FIG. 1.

FIG. 13 is a view for explaining the operation of a convey mechanism controller according to this embodiment.

FIG. 15 is a view for explaining an operation example (in case of one normal placement sensor) of the rack sampler upon placement of the rack according to this embodiment.

FIG. 18 is a view showing a convey example of the rack according to this embodiment.

DETAILED DESCRIPTION

In general, according to one embodiment, an automatic analyzer includes a convey mechanism, a driving unit, an error placement detection unit, and a controller. The convey mechanism configured to move a rack. The rack is configured to store a cuvette, along a predetermined linear moving direction. The driving unit drives the convey mechanism to intermittently move the rack along the moving direction. The error placement detection unit outputs an error placement signal when the error placement detection unit detects that a placement state of the rack on the convey mechanism corresponds to an error placement which does not allow the convey mechanism to normally convey the rack, and not to outputs the error placement signal when the error placement detection unit detects that the placement state does not correspond to the error placement. The controller controls the driving unit to stop a convey operation of the rack by the convey mechanism when the error placement signal is output and to execute the convey operation of the rack by the convey mechanism when the error placement signal is not output.

An automatic analyzer according to this embodiment will be described hereinafter with reference to the drawings. Note that this embodiment targets at a compact automatic analyzer suitable for measurements of the small number of samples.

(Overall Arrangement of Automatic Analyzer)

Figure 1:
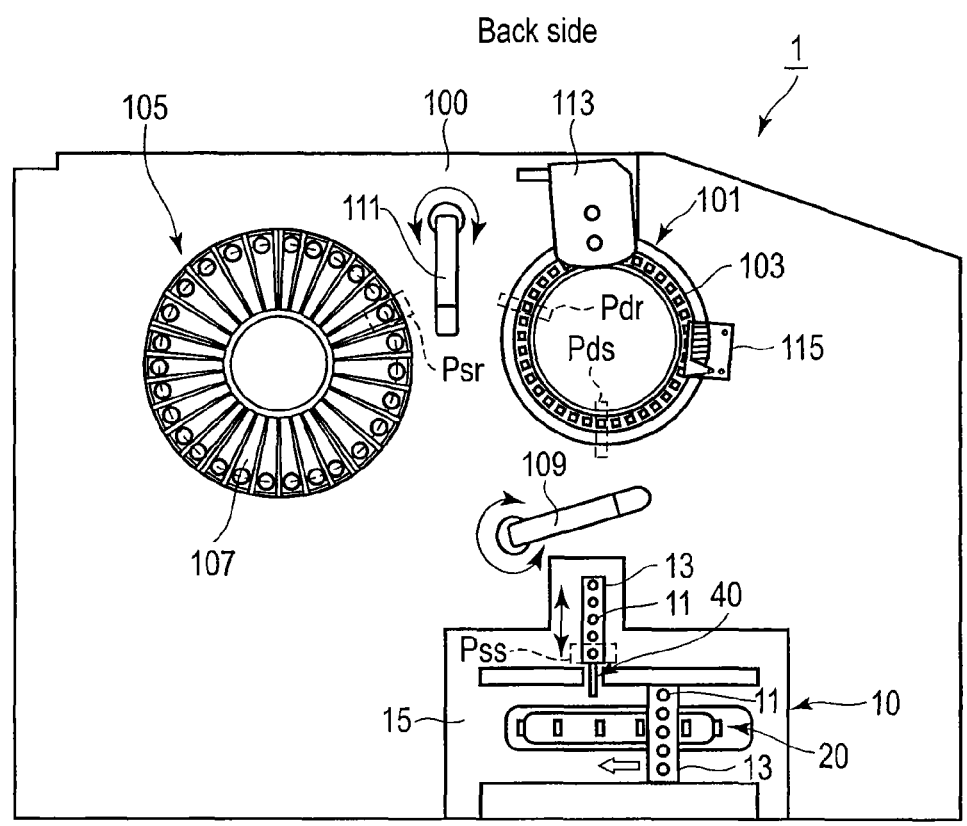
FIG. 1 is a view showing the outer appearance of an automatic analyzer according to this embodiment.

FIG. 1 is a plan view of an automatic analyzer 1 according to this embodiment. As shown in FIG. 1, the automatic analyzer 1 includes a stage 100 on an upper surface of a housing of itself. Note that in this embodiment, a side where the user stands with respect to the stage 100 will be referred to as a front side hereinafter, and a side opposite to the front side behind the stage 100 will be referred to as a back side hereinafter.

A reaction disc 101 is arranged at a predetermined position of the stage 100. The reaction disc 101 holds a plurality of reaction tubes 103 laid out in a circumferential pattern. The reaction disc 101 alternately and repetitively pivots and stops at predetermined time intervals. The reaction disc 101 rotates through a predetermined angle (for example, an angle for about ¼ round) by a single pivotal motion. The reaction disc 101 alternately and repetitively pivots and stops to place the reaction tubes 103 at all stop positions in the reaction disc 101.

On the front side of the stage 100, a rack sampler 10 is disposed. The rack sampler 10 moves a cuvette 11 which contains a sample to be measured to a sample suction position Pss. The cuvette 11 is detachably stored in a rack 13. The rack sampler 10 has a housing 15 required to hold respective mechanical elements. The housing 15 houses a convey mechanism 20 and pull-in mechanism 40. The convey mechanism 20 is a moving mechanism required to intermittently move (convey) the rack 13 along a predetermined linear moving direction (convey direction). An operation of the convey mechanism 20 which alternately and repetitively moves and stops to convey the rack 13 will be referred to as a convey operation hereinafter. The rack 13 is conveyed to a predetermined pull-in position Pp by the convey mechanism 20. The pull-in mechanism 40 is a moving mechanism required to reciprocally slide the rack 13 conveyed to the pull-in position Pp along a predetermined moving direction (slide direction). The pull-in mechanism 40 places the cuvette 11 which contains a sample to be measured at the sample suction position Pss by sliding the rack 13. Details of the rack sampler 10 will be described later.

A reagent storage 105 is disposed in the vicinity of the reaction disc 101. The reagent storage 105 holds reagent containers 107 which contain reagents. The reagent storage 105 pivots to locate a reagent container 107 which contains a reagent to be dispensed at a reagent suction position Psr.

A sample arm 109 is disposed between the reaction disc 101 and rack sampler 10. A sample probe (not shown) is attached to the distal end of the sample arm 109. The sample arm 109 pivots the sample probe along a rotational orbit about a rotational axis, and moves it upward and downward at a predetermined position. For example, the sample arm 109 locates the sample probe above the sample suction position Pss, and moves the sample probe downward into the cuvette 11. The sample probe which is moved downward sucks in a sample in the cuvette 11 by a predetermined amount. After the suction operation of the sample by the sample probe, the sample arm 109 moves the sample probe upward. Upon completion of the upward movement of the sample probe, the sample arm 109 pivots the sample probe along the rotational orbit, and locates it at a sample discharge position Pds on the reaction disc 101. After that, the sample probe discharges the sample into the reaction tube 103 disposed at the sample discharge position Pds.

A reagent arm 111 is arranged between the reaction disc 101 and reagent storage 105. A reagent probe (not shown) is attached to the distal end of the reagent arm 111. The reagent arm 111 pivots the reagent probe along a rotational orbit, and locates it at a reagent suction position Psr on the reagent storage 105. Next, the reagent arm 111 moves the reagent probe downward to enter it into a reagent bottle 107 disposed at a reagent suction position Psr. The reagent probe which has entered into the reagent bottle 107 sucks in a reagent by a predetermined amount. After completion of the suction operation of the reagent by the reagent probe, the reagent arm 111 moves the reagent probe upward. Upon completion of the upward movement of the reagent probe, the reagent arm 111 pivots the reagent probe along the rotational orbit, and locates it at a reagent discharge position Pdr on the reaction disc 101. After that, the reagent probe discharges the reagent into the reaction tube 103 disposed at the reagent discharge position Pdr.

A stirring mechanism 113 is arranged at a predetermined position on the outer circumference of the reaction disc 101. The stirring mechanism 113 includes a stirring bar. The stirring bar stirs the sample and reagent in the reaction tube 103 disposed at a stirring position on the reaction disc 101.

A photometry mechanism (not shown) is arranged inside the stage 100. The photometry mechanism causes a light source to continuously emit light, and continuously irradiates a photometry position (not shown) of the reaction disc 101 with light. The reaction tube 103 is pivoted by the reaction disc 101 so as to get across light with which the photometry position is irradiated. The photometry mechanism detects light transmitted through a liquid mixture of the sample and reagent in the reaction tube 103, and measures a light amount of the detected light.

A washing mechanism 115 is arranged at another predetermined position on the outer circumference of the reaction disc 101. The washing mechanism 115 includes a plurality of wash nozzles and dry nozzles. The washing mechanism 115 washes the reaction tube 103 located at a wash position (not shown) on the reaction disc 101 using the wash nozzles and dries it using the dry nozzles.

(Functional Arrangement of Rack Sampler)

The functional arrangement of the rack sampler 10 will be described below with reference to FIG. 2. FIG. 2 is a functional block diagram of the rack sampler 10. As shown in FIG. 2, the rack sampler 10 has the convey mechanism 20, a convey mechanism driving unit 22, an error placement detection unit 24, a normal placement detection unit 26, a convey mechanism controller 28, a warning unit 30, the pull-in mechanism 40, a pull-in mechanism driving unit 42, a code information reading unit 44, a pull-in mechanism controller 46, a storage unit 32, and a rack sampler controller 34.

The convey mechanism 20 intermittently conveys the rack 13 placed on a convey member of the convey mechanism 20 along the convey direction upon reception of a driving signal supplied from the convey mechanism driving unit 22. The convey mechanism driving unit 22 supplies the driving signal to the convey mechanism 20 according to a control signal from the convey mechanism controller 28. Note that the detailed structure of the convey mechanism 20 will be described later.

The error placement detection unit 24 detects whether or not a placement state of the rack 13 on the convey mechanism 20 corresponds to a placement in which the rack 13 cannot be normally conveyed by the convey mechanism 20 (to be referred to as an error placement hereinafter). When the error placement detection unit 24 detects that the placement state corresponds to the error placement, it outputs a signal which advises accordingly (to be referred to as an error placement signal hereinafter). On the other hand, when the error placement detection unit 24 detects that the placement state does not correspond to the error placement, it does not output any error placement signal, and outputs a signal which advises accordingly (to be referred to as a non-error placement signal hereinafter) instead. The error placement detection unit 24 is implemented by, for example, a transmission type optical sensor. In this case, the error placement detection unit 24 includes a light source which emits light, and a detector which detects light from the light source. The light source and detector are installed to sandwich a space region where at least a portion of the rack 13 enters only when the rack 13 is erroneously placed.

The normal placement detection unit 26 detects whether or not the placement state corresponds to a placement in which the rack 13 can be normally conveyed by the convey mechanism 20 (to be referred to as a normal placement hereinafter). When the normal placement detection unit 26 detects that the placement state corresponds to the normal placement, it outputs a signal which advises accordingly (to be referred to as a normal placement signal hereinafter). On the other hand, when the normal placement detection unit 26 detects that the placement state does not correspond to the normal placement, it does not output any normal placement signal, and outputs a signal which advises accordingly (to be referred to as a non-normal placement signal hereinafter) instead. The normal placement detection unit 26 is implemented by, for example, a transmission type optical sensor. In this case, the normal placement detection unit 26 includes a light source which emits light, and a detector which detects light from the light source. The light source and detector are installed to sandwich a space region where at least a portion of the rack 13 enters only when the rack 13 is normally placed.

Note that each of the error placement detection unit 24 and normal placement detection unit 26 is not limited to the transmission type optical sensor, and any other kinds of existing sensors such as a reflection type optical sensor, magnetic sensor, and weight sensor may be used as long as that sensor can detect an object included in a predetermined space region. The error placement detection unit 24 and normal placement detection unit 26 may be the sensors of the same type or of different types.

The convey mechanism controller 28 supplies the control signal to the convey mechanism driving unit 22 so as to intermittently convey the rack 13 along the convey direction. In this case, the convey mechanism controller 28 controls to execute and stop the convey operation in accordance with signals from the error placement detection unit 24 and normal placement detection unit 26. That is, when the error placement signal is output during a stop period in the convey operation, the convey mechanism controller 28 supplies the control signal to the convey mechanism driving unit 22 to stop the convey operation. That is, when the rack 13 is erroneously placed, the convey operation is automatically stopped. On the other hand, when no error placement signal is output but the non-error placement signal is output during the stop period in the convey operation, the convey mechanism controller 28 supplies the control signal to the convey mechanism driving unit 22 to execute the convey operation. That is, when the rack 13 is not erroneously placed, the convey operation is executed. In order to further enhance the safety, the convey mechanism controller 28 may use information as to whether or not the normal placement signal is output in judgment as to whether to stop or execute the convey operation. For example, when the error placement signal is not output (the non-error placement signal is output) and when the normal placement signal is output, the convey mechanism controller 28 supplies the control signal to the convey mechanism driving unit 22 to execute the convey operation. Otherwise, that is, when the error placement signal is output or when the error placement signal is not output (the non-error placement signal is output) and when the normal placement signal is output (the non-normal placement signal is output), the convey mechanism controller 28 supplies the control signal to the convey mechanism driving unit 22 to stop the convey operation.

When the convey mechanism controller 28 stops the convey operation, the warning unit 30 generates a warning that advises accordingly. More specifically, when the error placement detection unit 24 outputs the error placement signal, the warning unit 30 gives, to the user, a warning indicating that the rack 13 is not normally placed at a position suitable for conveyance. Furthermore, when the error placement detection unit 24 does not output any error placement signal but the normal placement detection unit 26 does not output any normal placement signal, the warning unit 30 gives, to the user, a warning indicating the same contents. Devices used to generate a warning include, for example, every devices such as a display 301, loudspeaker 303, and lamp 305, which are perceivable by the user's five senses. The display 301 may display, for example, a message "place a rack at a normal position". The loudspeaker 303 may output, for example, an audible message "place a rack at a normal position" or warning sound. The lamp 305 may be, for example, turned on or flickered so as to call attention to the user.

The pull-in mechanism 40 reciprocally slides the rack 13 conveyed to the pull-in position Pp along the slide direction upon reception of a driving signal supplied from the pull-in mechanism driving unit 42. The pull-in mechanism driving unit 42 supplies the driving signal to the pull-in mechanism 40 according to a control signal from the pull-in mechanism controller 46. Note that the detailed structure of the pull-in mechanism 40 will be described later.

The code information reading unit 44 reads code information printed on the rack 13 placed at the pull-in position Pp of the housing 15 to recognize an identification number of the rack 13. The identification number is supplied to the pull-in mechanism controller 46.

The pull-in mechanism controller 46 supplies the control signal to the pull-in mechanism driving unit 42 so as to locate the cuvette 11 which contains a sample to be measured at the sample suction position Pss by moving the rack 13 along the slide direction. The cuvette which contains the sample to be measured will be referred to as a measurement container hereinafter. More specifically, the pull-in mechanism controller 46 collates the identification number from the code information reading unit 44 with order information stored in the storage unit 32. The order information includes, for each measurement item, the number of the rack 13 which stores the measurement containers 11 according to the measurement item and position numbers of the measurement containers in the rack 13. Upon collation between the identification number and order information, the position of each measurement container 11 in the rack 13 is specified. The pull-in mechanism controller 46 supplies the control signal to the pull-in mechanism driving unit 42 so as to locate the measurement container 11 at the specified position at the sample suction position Pss. Thus, the pull-in mechanism 40 is driven, and each measurement container 11 is placed at the sample suction position Pss. After samples in all the measurement containers 11 stored in the pulled-in rack 13 are sucked in, the pull-in mechanism controller 46 supplies the control signal to the pull-in mechanism driving unit 42 so as to locate the rack 13 at the pull-in position Pss. Thus, the rack 13 is returned to the pull-in position Pss.

The storage unit 32 stores order information, which is set in advance by the user. The user inputs, the order information via, for example, a console (not shown) of the automatic analyzer 1. The storage unit 32 stores, for each measurement item, the number of the rack 32 which stores measurement containers 11 according to the measurement item and position umbers of the measurement containers 11 in the rack 13 in association with each other.

The rack sampler controller 34 functions as a core of the rack sampler 10.

With this functional arrangement, the rack sampler 10 detects the placement state of the rack 13 on the convey mechanism 20, and when the placement state of the rack 13 corresponds to the error placement which is not suitable for conveyance, it automatically stops the convey operation. On the other hand, when the placement state of the rack 13 corresponds to the normal placement suitable for conveyance, or does not correspond to the error placement, the rack sampler 10 automatically executes the convey operation.

The detailed structure of the rack sampler 10 which implements the aforementioned mechanism will be described below.

(Structure of Rack)

Figure 3:
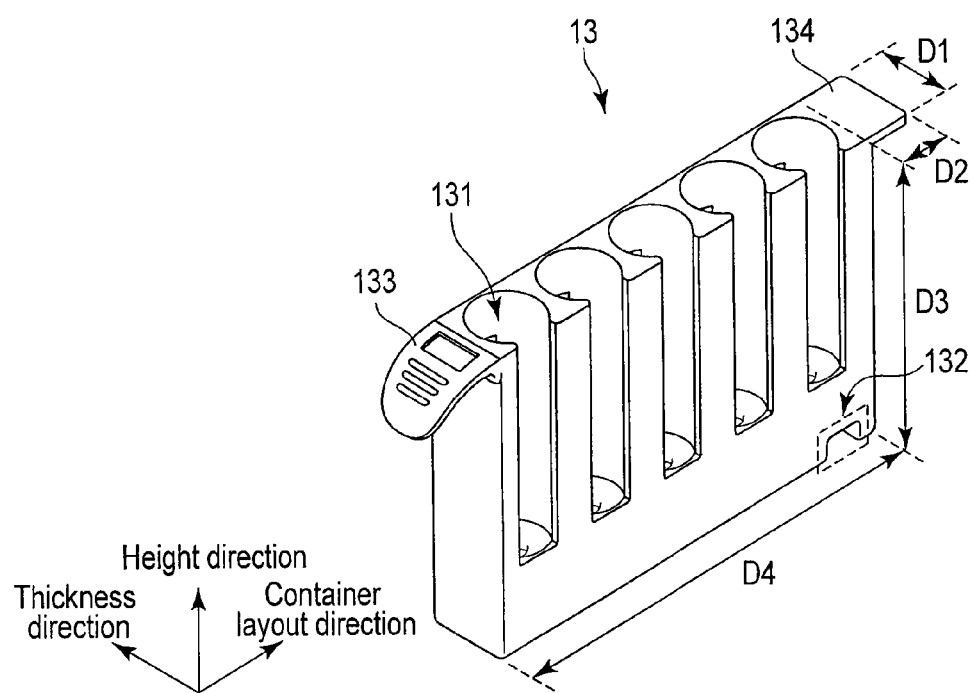
FIG. 3 is a perspective view of a rack according to this embodiment.

The structure of the rack 13 used in the rack sampler 10 will be described first. FIG. 3 is a perspective view of the rack 13. The rack 13 is formed by, for example, injection molding using a resin as a material. The rack 13 has a plurality of storage spaces 131 which can detachably store cuvettes. The cuvettes are stored in the respective storage spaces 131. The plurality of storage spaces 131 are linearly laid out. In this manner, the rack 13 has a structure which can store a relatively small number of cuvettes to attain a size reduction. Therefore, the rack 13 has a relatively small bottom area, and readily falls at the time of conveyance.

Note that the layout direction of the storage spaces 131 will be referred to as a container layout direction hereinafter, an axial direction of the storage space 131 will be referred to as a height direction hereinafter, and a direction perpendicular to both the container layout direction and height direction will be referred to as a thickness direction hereinafter.

A notch 132 is formed at one end of the bottom portion of the rack 13 along the container layout direction. The notch 132 is formed to allow the pull-in mechanism 40 to pull in the rack 13. The rack 13 has a grip portion 133 at one end of the top end portion along the container layout direction and a projecting portion 134 at the other end thereof. The grip portion 133 is gripped by the user when he or she holds the rack 13. The projecting portion 134 functions as, for example, an object to be detected by the normal placement detection unit 26.

In order to recognize a position of a specific cuvette in the rack 13, a position number is adhered to the vicinity of a cuvette insertion port of the rack 13. Although not shown, in order to identify the rack 13, a code such as a one-dimensional code or two-dimensional code is adhered to a predetermined position of the rack 13.

In the following description, let D1 be a length of the projecting portion 134 in the thickness direction, D2 be that of the projecting portion 134 in the container layout direction, D3 be that of the rack 13 in the height direction, and D4 be that of a main body portion of the rack 13 except for the grip portion 133 and projecting portion 134 in the container layout direction.

(Overall Structure of Rack Sampler)

Figure 4:
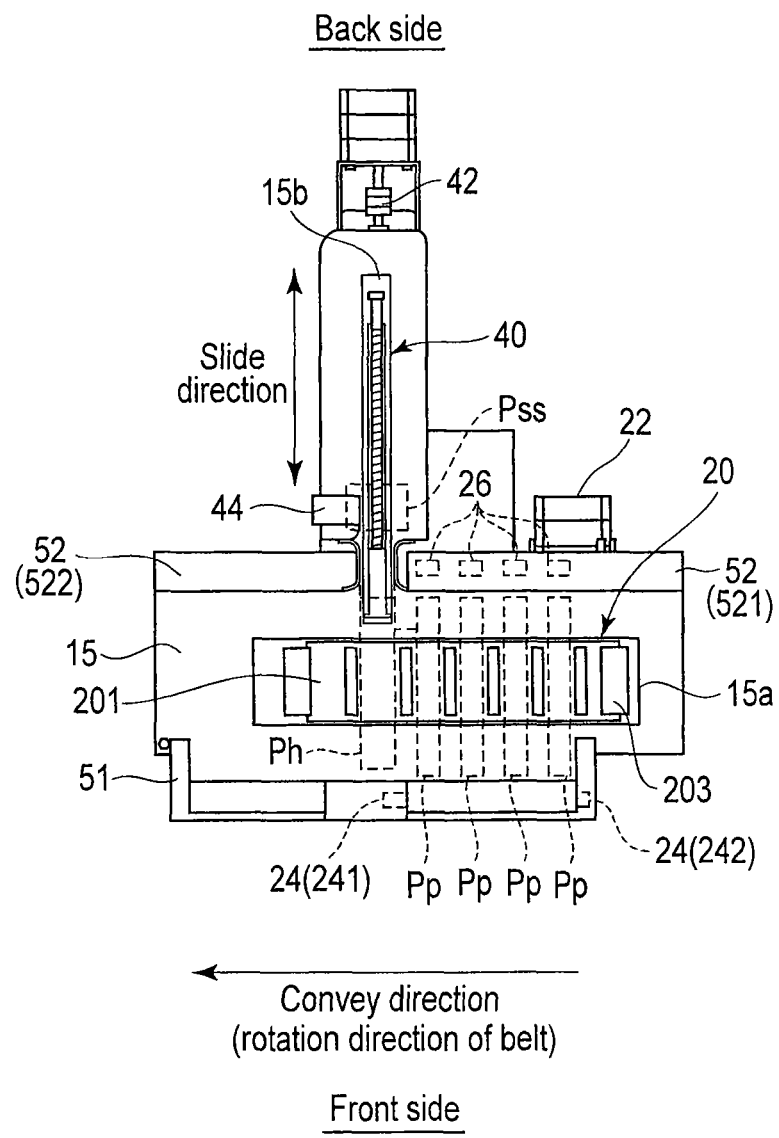
FIG. 4 is a plan view of a rack sampler in FIG. 1.
Figure 5:
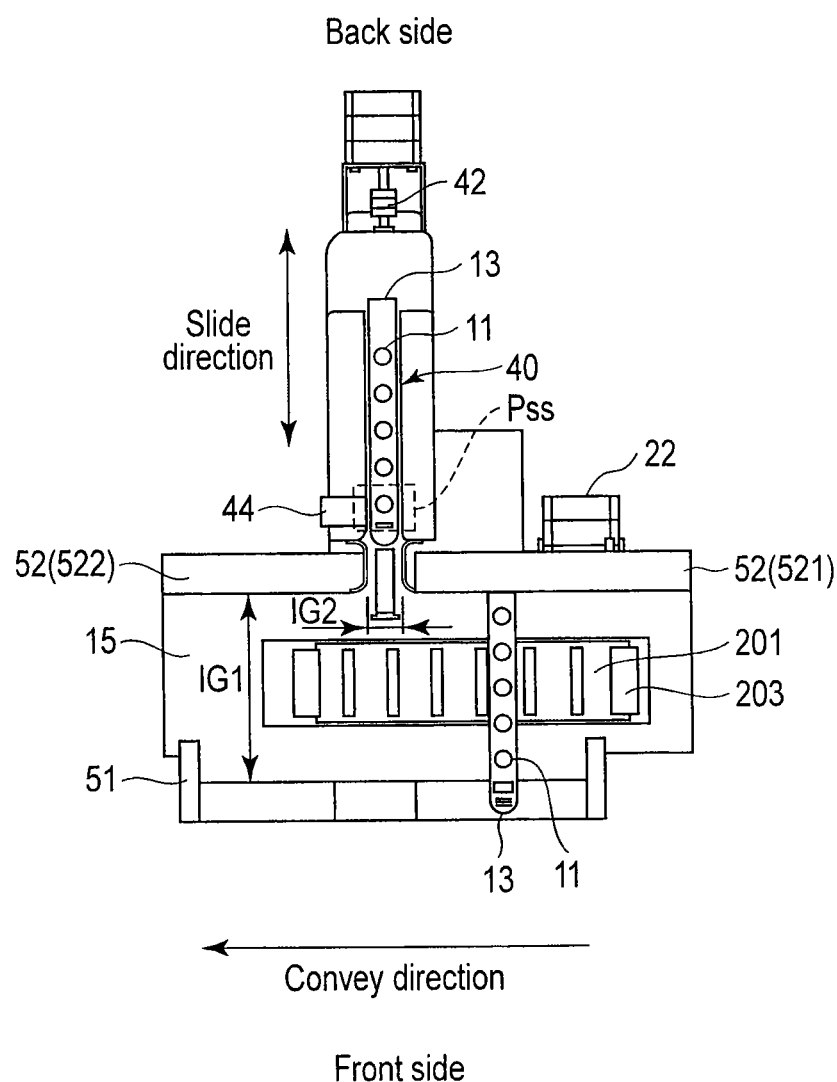
FIG. 5 is a plan view of the rack sampler in FIG. 4 on which the rack according to this embodiment is placed.

The structure of the rack sampler 10 will be described below. FIG. 4 is a plan view of the rack sampler 10. FIG. 5 is a plan view of the rack sampler 10 on which the rack 13 is placed. FIG. 6 is a perspective view of a convey mechanism portion included in the rack sampler 10. FIG. 7 is a perspective view of the convey mechanism portion on which the rack 13 is placed.

The housing 15 has an opening 15a for the convey mechanism 20 on the front side. The opening 15a houses the convey mechanism 20. For example, the convey mechanism 20 is realized by a belt conveyor. More specifically, the convey mechanism 20 has an annular belt 201 and rotors (not shown). The annular belt 201 functions as a convey member of the rack 13. The rotors are arranged at two ends of a circular ring of the belt 201. Each rotor is rotated by receiving the driving signal supplied from the aforementioned convey mechanism driving unit (motor) 22. Upon rotation of the rotors, the belt 201 moves along the convey direction.

The belt 201 alternately and repetitively moves and stops along the convey direction upon rotation and stopping of the rotors. A plurality of projections 203 are formed on an outside surface of the belt 201. Each projection 203 has, for example, a tabular shape. The respective projections 203 are parallelly laid out along a horizontal direction perpendicular to the convey direction. A space between the two neighboring projections 203 is set to be slightly larger than the width of the rack 13 in the thickness direction. The rack 13 is placed between the neighboring projections 203. In this manner, the projections 203 function as positioning guides of the rack 13 to be placed on the convey mechanism 20. The housing 15 is set with a plurality of rack placement positions Pp and a single pull-in position Ph. In FIG. 4 and the like, for example, four rack placement positions Pp are assured, and five racks 13 can be simultaneously placed in consideration of the pull-in position Ph. The stop position of the belt 201 and a single moving amount are set so that the rack placement positions Pp and pull-in position Ph are located between the neighboring projections 203 when the belt 201 is stopped.

In order to prevent the rack 13 from falling, the belt 201 is arranged on the inner side of the housing 15 so that the projections 203 project outside the surface of the housing 15. In other words, even when the rack 13 is placed between the neighboring projections 203, the belt 201 is arranged on the inner side of the housing 15 so as to prevent the rack 13 from contacting the belt 201. Note that when the rack 13 is placed between the neighboring projections 203, a portion, which does not face the opening 21a, of the bottom surface of the rack 13 typically contacts the surface of the housing 15. Upon rotation of the belt 201, each projection 203 pushes the lower portion of the rack 13 placed between the neighboring projections 203 along the convey direction. In this manner, the rack 13 moves along the convey direction when it is pushed by the projection 203. The racks 13 placed between the neighboring projections 203 are placed in turn at the respective placement positions Pp while they alternately and repetitively move and stop.

The housing 15 is arranged with a guide 51 on the front side of the convey mechanism 20 (to be referred to as a front-side guide hereinafter) and a guide 52 on the back side thereof (to be referred to as a back-side guide hereinafter) to guide conveyance of the rack 13 in the convey direction. The front-side guide 51 and back-side guide 52 are installed to be parallel to the convey direction. A gap IG1 between the front-side guide 51 and back-side guide 52 is designed according to the length D4 of the main body portion of the rack 13 along the container layout direction. For example, the gap IG1 is set to be slightly longer than the length D4 of the rack 13. Based on such positional relationship between the front-side guide 51 and back-side guide 52, position variations of the rack 13 in the right-and-left direction (the horizontal direction perpendicular to the convey direction) at the time of conveyance are structurally limited.

For example, as shown in FIGS. 6 and 7, the back-side guide 52 has a slit 52s extending parallelly along the convey direction. The slit 52s is set at a position where the projecting portion 134 can be inserted when the rack 13 is properly placed on the convey mechanism 20. The rack 13 moves along the convey direction while its projecting portion 134 is inserted in the slit 52s. The slit 52s has a role of structurally limiting position variations of the rack 13 along the vertical direction at the time of conveyance.

The back-side guide 52 includes a first back-side guide 521 and second back-side guide 522. The first back-side guide 521 and second back-side guide 522 are installed to be spaced by a gap IG2. The position of the gap IG2 is set so that the position of the gap IG2 and the pull-in position Ph along the convey direction overlap each other. The gap IG2 is set to be longer than the length D1 of the rack 13 so as to allow the rack 13 to pass through the gap IG2. The first back-side guide 521 is arranged to guide the rack 13 before it is pulled in, and the second back-side guide 522 is arranged to guide the rack 13 after it is pulled in.

When the user places the rack 13, he or she puts the rack 13 on the front-side guide 51, pushes the rack 13 from the front-side guide 51 side toward the first back-side guide 521 side, and inserts the projecting portion 134 of the rack 13 into the slit 52s. As described above, the positions of the front-side guide 51 and back-side guide 52 are set so as to prevent the other end of the rack 13 (that is, the grip portion 133 side) from riding on the front-side guide 51 in a state in which the rack 13 is inserted into the slit 52s.

Figure 8:
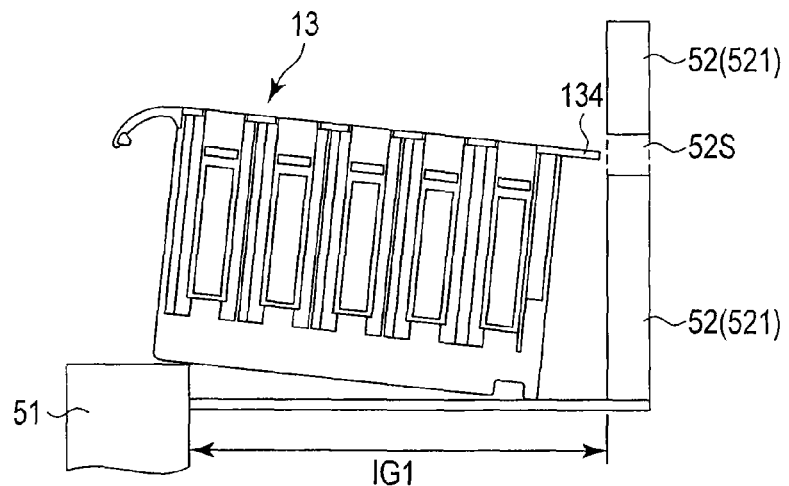
FIG. 8 is a view showing placement (error placement) of the rack which is improper for conveyance according to this embodiment.
Figure 9:
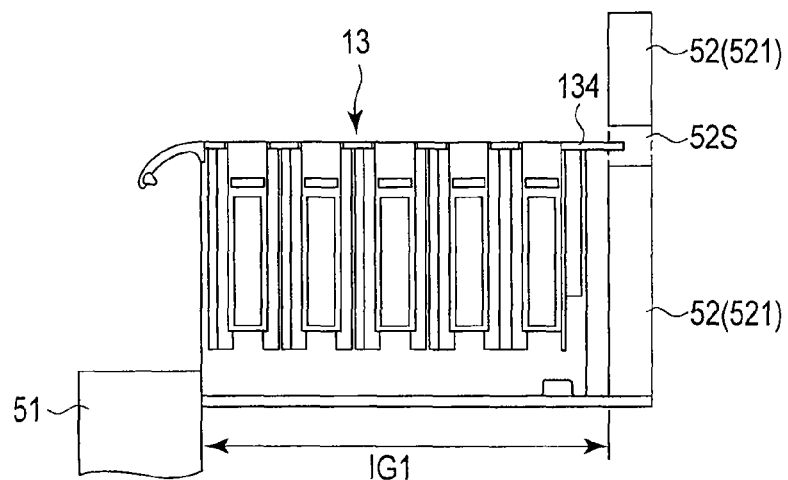
FIG. 9 is a view showing placement (normal placement) of the rack which is proper for conveyance according to this embodiment.

That is, as shown in FIG. 8, when the rack 13 rides on the front-side guide 51, the projecting portion 134 of the rack 13 is not inserted in the slit 52s due to the structural limitation. When the projecting portion 134 is not inserted in the slit 52s, the rack 13 falls at a high possibility when it is conveyed. Therefore, this placement state is a typical example of the error placement which is improper for conveyance. On the other hand, as shown in FIG. 9, when the rack 13 does not ride on the front-side guide 51, the projecting portion 134 of the rack 13 is inserted in the slit 52s. When the projecting portion 134 is inserted in the slit 52s, the rack 13 falls at a low possibility when it is conveyed. Therefore, this placement state is the normal placement which is proper for conveyance.

In order to mechanically detect whether or not the rack 13 is erroneously placed, a sensor which functions as the aforementioned error placement detection unit 24 (error placement sensor) is attached to the front-side guide 51. One error placement sensor 24 need only be arranged for the plurality of placement positions Pp. To the back-side guide 52, a sensor which functions as the aforementioned normal placement detection unit 26 (normal placement sensor) is attached so as to mechanically detect whether or not the rack 13 is normally placed. The normal placement sensor 26 is arranged for each placement position Pp.

The rack 13 is conveyed to the pull-in position Ph while being repetitively moved and stopped by the convey mechanism 20. The rack 13 placed at the pull-in position Ph is pulled in toward the back side by the pull-in mechanism 40 along the slide direction to pass through a gap between the first back-side guide 521 and second back-side guide 522.

The pull-in mechanism 40 is arranged in an opening 25b formed on the back side of the housing 15. The pull-in mechanism 40 is a moving mechanism for reciprocally and linearly moving the rack 13 along the slide direction. This slide direction is set in a horizontal direction perpendicular to the convey direction.

Figure 10:
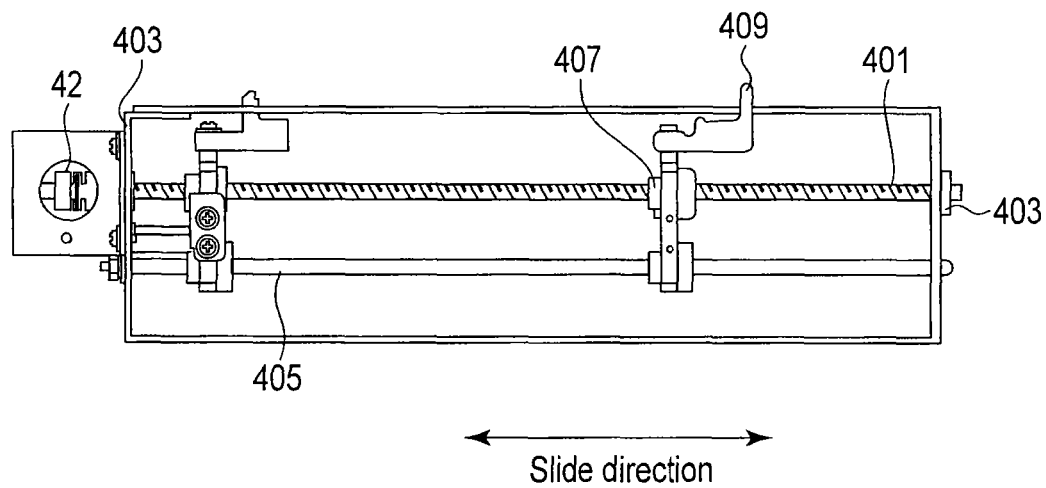
FIG. 10 is a side view of a pull-in mechanism included in the rack sampler in FIG. 1.

FIG. 10 is a side view of the pull-in mechanism 40. As shown in FIG. 10, the pull-in mechanism 40 is realized by a ball screw. That is, the pull-in mechanism 40 has a screw shaft 401, support members 403, a guide rail 405, a slider 407, and a hook 409. The screw shaft 401 is installed in the housing 15 so that its shaft center extends parallel to the slider direction. The two ends of the screw shaft 401 are rotatably supported by the support members 403. The screw shaft 401 is rotated upon rotation of a rotation shaft of the pull-in mechanism driving unit (motor) 42. In the housing 15, the guide rail 405 is installed to be parallel to the shaft center of the screw shaft 401. The slider 407 has a through hole formed with a groove (female screw) threadably engaging with that (male screw) of the screw shaft 401. The slider 407 is screwed on the screw shaft 401. The slider 407 slides along the shaft center direction (slider direction) of the screw shaft 401 upon rotation of the screw shaft 401. The hook 409 is attached to the slider 407. The distal end portion of the hook 409 is exposed outside the housing 15 via an opening 15b. The hook 409 slides along the slide direction together with the slider 407 upon rotation of the screw shaft 401. The distal end portion of the hook 409 has a shape that can hook on the notch 132 of the rack 13. When the screw shaft 401 is rotated while the hook 409 hooks on the notch 132, the rack 13 slides along the slide direction.

A reader which functions as the aforementioned code information reading unit 44 is arranged in the vicinity of the pull-in position Ph. The reader 44 optically reads a one-dimensional code or two-dimensional code adhered to the rack 13, and specifies an identification number of the rack from the read code information. The specified identification information is transmitted to the pull-in mechanism controller 46.

With this structure, the pull-in mechanism 40 pulls in the rack 13 placed at the pull-in position Ph, and places the cuvette (measurement container) 11 which contains a sample to be measured at the sample suction position Pss under the control of the pull-in mechanism controller 46. After the sample is sucked in, the pull-in mechanism 40 pushes out the rack 13 to locate it at the pull-in position Ph again. The rack 13 placed at the pull-in position Ph is pushed out by the convey mechanism 20 outside the convey mechanism 20 along the convey direction. The pushed-out rack 13 is recovered by the user.

(Details of Front-Side Guide, Error Placement Sensor, Back-Side Guide, and Normal Placement Sensor)

Figure 11:
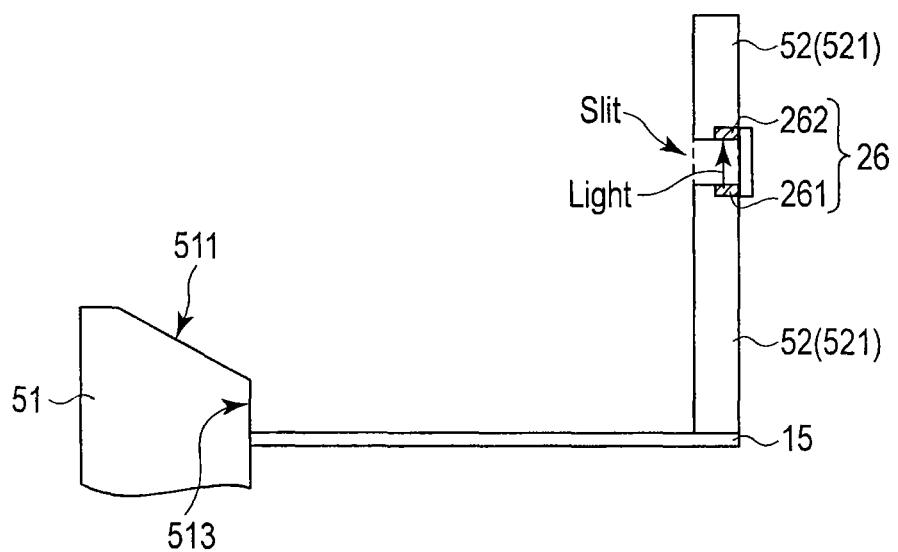
FIG. 11 is a side view a front-side guide and back-side guide included in the rack sampler in FIG. 1.

FIG. 11 is a side view of the front-side guide 51 and back-side guide 52 at the placement position Pp. FIG. 12 is a plan view of the front-side guide 51 and back-side guide 52. Note that FIGS. 11 and 12 do not illustrate the convey mechanism 20 for the sake of descriptive convenience.

The front-side guide 51 includes a slope portion 511 and wall portion 513. The slope portion 511 is formed to aid the user to normally place the rack 13. For this purpose, the slope angle of the slope portion 511 may be set to be, for example, an angle which allows the rack 13 to be slidable toward the convey mechanism 20 by the self weight. By setting the slope angle in this way, the rack 13 can be prevented from being kept placed on the slope portion 511 at the time of placement. Note that the slope angle may be set in consideration of either the weight of the rack 13 which does not store any cuvette 11 or that of the rack 13 which stores the cuvettes 11. The wall portion 513 is formed below the slope portion 511. The wall portion 513 has a wall surface roughly perpendicular to the surface of the housing 15. A step is formed between the slope portion 511 and housing 15 via the wall portion 513. The wall portion 513 is arranged to guide conveyance of the rack 13 in the convey direction.

The error placement sensor 24 is arranged on the slope portion 511. The error placement sensor 24 is arranged to optically detect if the rack 13 rides on the slope portion 511. More specifically, the error placement sensor 24 includes a light source 241 and detector 242. The light source 241 and detector 242 are disposed to sandwich a space region above the slope 511 where the rack 13 enters in only a state in which the projecting portion 134 is not inserted into the slit 52s. The light source 241 and detector 242 are disposed at positions where they can detect the error placements of a plurality of racks 13 by a pair. For example, the light source 241 and detector 242 are arranged at the two ends of the slope portion 511 along the convey direction.

The light source 241 repetitively emits light. The detector 242 outputs an electrical signal corresponding to an ON level during a detection period of light from the light source. More specifically, when the rack 13 does not ride on the slope portion 511, since light from the light source 241 is not intercepted by the rack 13, the detector 242 outputs the electrical signal corresponding to the ON level. That is, the electrical signal corresponding to the ON level corresponds to the aforementioned non-error placement signal. On the other hand, during a non-detection period of light emitted by the light source 241, the detector 242 outputs an electrical signal corresponding to an OFF level. More specifically, when the rack 13 rides on the slope portion 511, since light from the light source 241 is intercepted by the rack 13, the detector 242 outputs the electrical signal corresponding to the OFF level. That is, the electrical signal corresponding to the OFF level corresponds to the aforementioned error placement signal.

The back-side guide 52 is formed with the slit 52s in which the projecting portion 134 of the rack 13 is to be inserted, as described above. The slit 52s is formed at a position where the projecting portion 134 of the rack 13 can be inserted when the rack 13 is placed between the wall portion 512 and back-side guide 52.

A plurality of normal placement sensors 26 respectively corresponding to the plurality of placement positions Pp are provided to the back-side guide 52. Each normal placement sensor 26 is arranged to optically detect whether or not the projecting portion 134 is inserted in the slit 52s corresponding to the placement position Pp of the rack 13. More specifically, each normal placement sensor 26 has a light source 261 and detector 262. The light source 261 and detector 262 are arranged on the back-side guide 52 to face each other and to sandwich the slit 52s between them. More specifically, the light source 261 and detector 262 are disposed to sandwich a space region in the slit 52s in which the projecting portion 134 enters when the rack 13 is placed between the wall portion 513 and back-side guide 52.

The light source 261 repetitively emits light. The detector 262 outputs an electrical signal corresponding to an ON level during a detection period of light from the light source. More specifically, when the projecting portion 134 is not inserted in the slit 52s corresponding to the placement position Pp, since light from the light source 261 is not intercepted by the projecting portion 134, the detector 262 outputs the electrical signal corresponding to the ON level. That is, the electrical signal corresponding to the ON level corresponds to the aforementioned non-normal placement signal. On the other hand, the detector 262 outputs an electrical signal corresponding to an OFF level during a non-detection period of light emitted by the light source 261. More specifically, when the projecting portion 134 is inserted into the slit 52s corresponding to the placement position Pp, since light from the light source 261 is intercepted by the projecting portion 134, the detector 262 outputs the electrical signal corresponding to the OFF level. That is, the electrical signal corresponding to the OFF level corresponds to the aforementioned normal placement signal.

Signals from the error placement sensor 24 and normal placement sensors 26 are repetitively supplied to the convey mechanism controller 28. While the convey mechanism 20 is active, a convey period and stop period of the belt 201 are alternately repeated. When the error placement signal is output, the convey mechanism controller 28 controls the convey mechanism driving unit 22 to immediately stop the convey operation of the convey mechanism 20. For example, when an object such as the rack 13 rides on the slope portion 511 during the convey period of the rack 13, the convey operation can be immediately stopped. When the rack 13 cannot be placed satisfactorily at the time of placement and is kept riding on the slope portion 511, the convey operation of the next convey period can be aborted.

When the non-error placement signal is output and the normal placement signal is output during the stop period in the convey operation, the convey mechanism controller 28 controls the convey mechanism driving unit 22 to continue or start the convey operation of the convey mechanism 20. In this case, when the normal placement signal is output, the convey mechanism 20 may be immediately driven. Or the convey mechanism 20 may be driven to have, as a trigger, a fact that the next convey period is reached. When the convey mechanism 20 is driven to have, as a trigger, the fact that the next convey period is reached, the belt 201 is moved in the next convey period when the non-error placement signal is output and the normal placement signal is output at the end of each stop period. Even when the non-error placement signal is output and the normal placement signal is output in the middle of the stop period, the belt 201 is not moved during the next convey period when the non-error placement signal is output and the normal placement signal is not output at the end of the stop period. Therefore, only when the rack 13 is normally placed to be proper for conveyance, the convey operation can be executed.

In practice, signals are supplied from the plurality of normal placement sensors 26. Therefore, when the non-error placement signal is output from the error placement sensor 24 and the normal placement signal is output from at least one of the plurality of normal placement sensors 26, the convey mechanism controller 28 can execute the convey operation. The effectiveness of this rule will be verified below.

For example, when the racks 13 are properly placed at all of the plurality of placement positions, as shown in FIG. 13, the convey operation should be executed. In this case, since light from the light source of the error placement sensor 24 reaches the detector, the error placement sensor 24 outputs the non-error placement signal. Since light from the light source of each normal placement sensor 26 is intercepted by the projecting portion 134 of each rack 13, each normal placement sensor 26 outputs the normal placement signal. Therefore, since the error placement sensor 24 outputs the non-error placement signal and at least one of the plurality of normal placement sensors 26 outputs the normal placement signal, the convey mechanism controller 28 can appropriately execute the convey operation according to the actual placement states of the racks 13.

Figure 14:
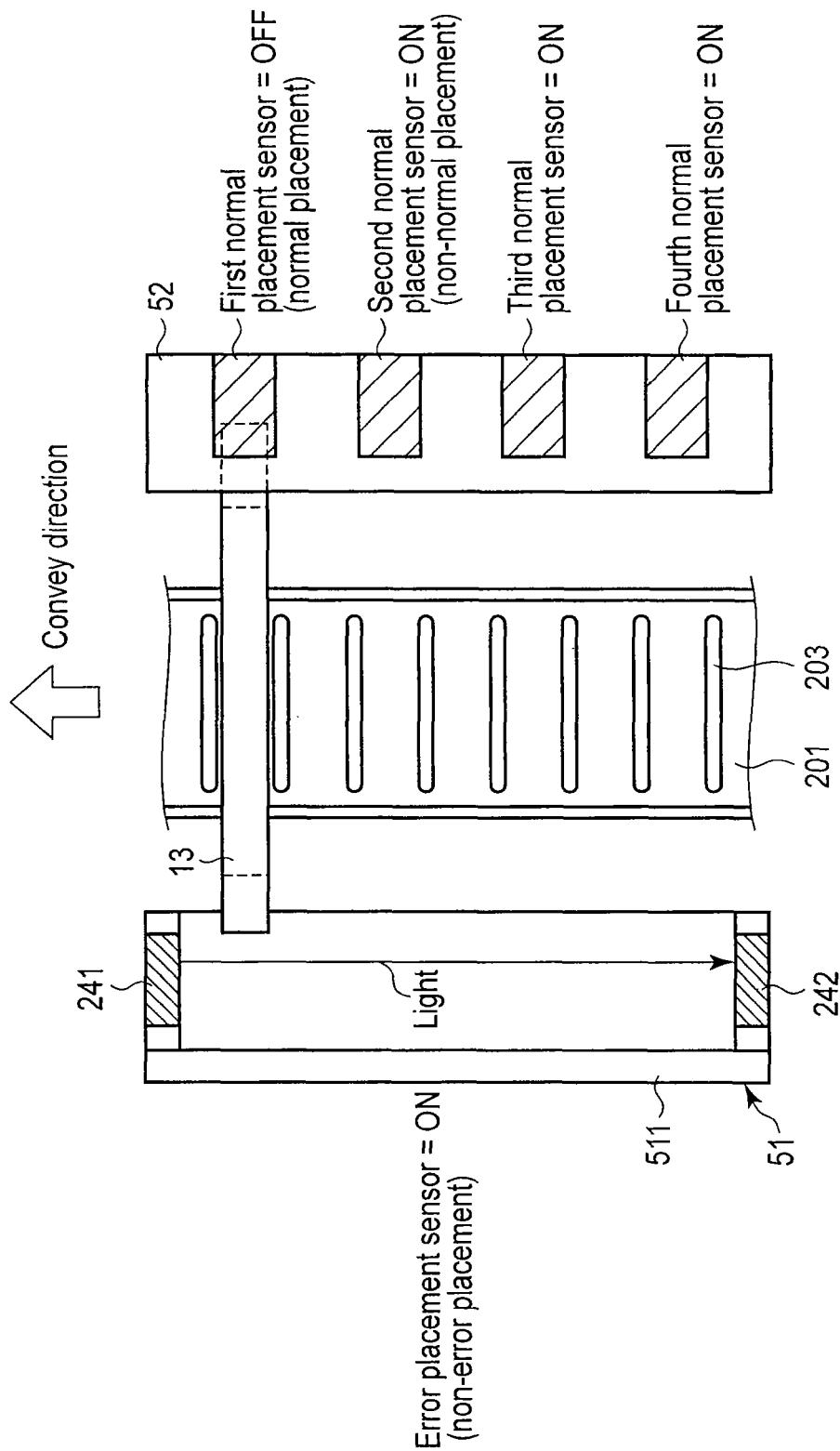
FIG. 14 is another view for explaining the operation of the convey mechanism controller according to this embodiment.

Also, for example, the racks 13 are often placed at not all the placement positions, as shown in FIG. 14. For example, assume that the rack 13 is properly placed at one placement position, and the rack 13 is not placed at the remaining three placement positions. In this case, the number of samples to be measured is merely small, and the convey operation should be executed. Since the placement state of the placed rack 13 corresponds to the normal placement, the error placement sensor 24 outputs the non-error placement signal. The first normal placement sensor 26 provided to the slit 52s corresponding to the placement position where the rack 13 is placed outputs the normal placement signal, and the remaining three normal placement sensors 26 output the non-normal placement signals. Therefore, since the error placement sensor 24 outputs the non-error placement signal and at least one of the plurality of normal placement sensors 26 outputs the normal placement signal, the convey mechanism controller 28 can judge that the convey operation is properly executed according to the actual placement state of the rack 13.

As can be seen from the verification results of these two placement examples, the rule that the convey operation is executed when the error placement sensor 24 outputs the non-error placement signal and at least one of the plurality of normal placement sensors 26 outputs the normal placement signal has the effectiveness.

Therefore, the rack sampler 10 according to this embodiment can convey the racks 13 after it places the racks 13 at accurate positions on the convey mechanism 20.

(Operation Example of Rack Sampler Upon Placement of Rack)

Figure 16:
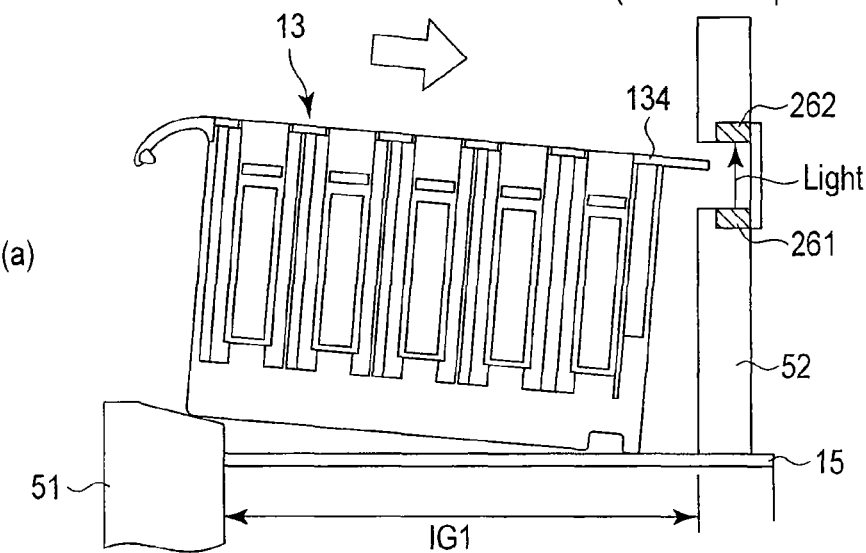
FIG. 16 is another view for explaining an operation example (in case of one normal placement sensor) of the rack sampler upon placement of the rack according to this embodiment.
Figure 16:
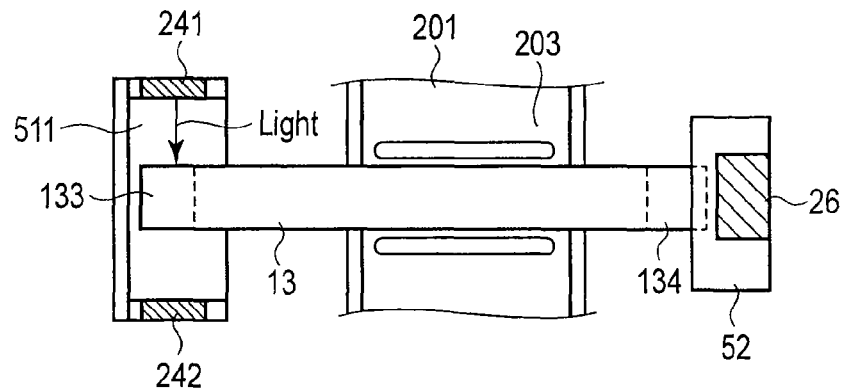
Figure 17:
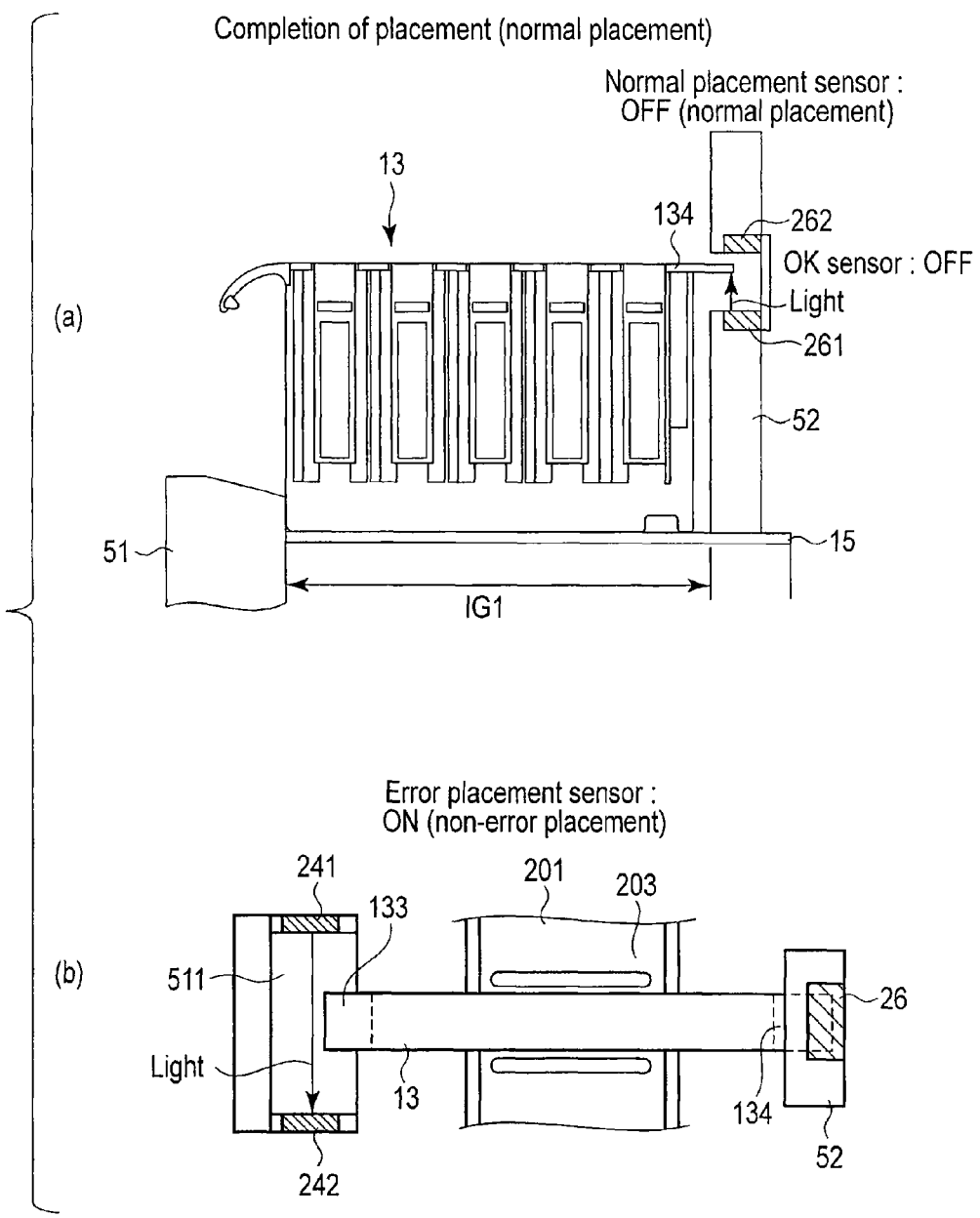
FIG. 17 is still another view for explaining an operation example (in case of one normal placement sensor) of the rack sampler upon placement of the rack according to this embodiment.

An operation example of the rack sampler 10 upon placement of the racks will be described below with reference to FIGS. 15, 16, and 17. Note that (a) of each of FIGS. 15, 16, and 17 is a side view, and (b) is a plan view. Assume that one normal placement sensor 26 is arranged for the sake of simplicity.

As shown in FIG. 15, the user puts the rack 13 on the front-side guide 51 and pushes it from the front-side guide 51 side toward the back-side guide 521 side when he or she places the rack 13. The reason why the rack 13 is placed by pushing is that the rack 13 cannot be placed from a position immediately above the belt 201 since the total length of the rack 13 (the length of the rack 13 including the grip portion 133 and projecting portion 134 along the container layout direction) is larger than the gap IG1 between the front-side guide 51 and back-side guide 52. When the user insufficiently pushes the rack 13 and a portion of the rack 13 rides on the slope portion 511, the convey operation should be stopped since the rack 13 cannot be normally conveyed. Light from the light source 241 of the error placement sensor 24 is intercepted by the rack 13 since the rack 13 rides on the slope portion 511. Therefore, the detector 242 of the error placement sensor 24 outputs the error placement signal. On the other hand, light from the light source 261 of the normal placement sensor 26 reaches the detector 262 of the normal placement sensor 26 since the projecting portion 134 is not inserted into the slit 52s. Therefore, the detector 262 outputs the non-normal placement signal. In this manner, since the error placement signal is supplied from the error placement sensor 24 and the non-normal placement signal is supplied from the normal placement sensor 26, the convey mechanism controller 28 stops the convey operation. In this case, the warning unit 30 informs the user of an error placement warning using the display 301, loudspeaker 303, or lamp 305.

When the user keeps pushing the rack 13, as shown in FIG. 16, the rack 13 begins to slide on the slope 511 by the self weight. Even in this state, since the rack 13 rides on the slope portion 511, the convey operation cannot be normally executed in this state. Therefore, the convey operation should be stopped. In this case, the error placement sensor 24 outputs the error placement signal since light from the light source 241 is intercepted by the rack 13. Also, the normal placement sensor 26 outputs the non-normal placement signal since light from the light source 261 is not intercepted. Therefore, the convey mechanism controller 28 continues to stop the convey operation, and the warning unit 30 informs the user of an error placement warning.

Note that the user may often place the rack 13 while holding up the grip portion 133. In this case, the error placement sensor 24 becomes insignificant, but the normal placement sensor 26 normally performs detection. That is, light from the light source 241 of the error placement sensor 24 is not intercepted by the rack 13, and reaches the detector 242. Therefore, the error placement sensor 24 outputs the non-error placement signal. However, since the projecting portion 134 is not inserted into the slit 52s, the normal placement sensor 26 outputs the non-normal placement signal. Therefore, the convey mechanism controller 28 stops the convey operation of the convey mechanism 20, and the warning unit 30 informs the user of an error placement warning.

When the user further keeps pushing the rack 13, as shown in FIG. 17, the rack 13 slips from the slope portion 511 and drops on the housing 15, and the projecting portion 134 of the rack 13 is inserted into the slit 52s. In this case, since the rack 13 does not ride on the slope portion 511 and the projecting portion 134 is inserted into the slit 52s, the rack 13 can be normally conveyed. Therefore, the convey operation should be executed. In case of this placement state, since light from the light source 241 is not intercepted by the rack 13, the error placement sensor 24 outputs the non-error placement signal. Light from the light source 261 is intercepted by the projecting portion 134 and does not reach the detector 262. Therefore, the normal placement sensor 26 outputs the normal placement signal. In this manner, since the error placement sensor 24 outputs the non-error placement signal and the normal placement sensor 26 outputs the normal placement signal, the convey mechanism controller 28 executes the convey operation.

CONVEY EXAMPLE OF RACK

When the rack 13 is properly placed, the convey mechanism controller 28 executes the convey operation.

FIG. 18 shows a convey example of the rack 13. As shown in FIG. 18, the properly placed rack 13 is conveyed in a state in which the projecting portion 134 is inserted into the slit 52s. Also, the properly placed rack 13 is sandwiched between the front-side guide 51 and back-side guide 52. Furthermore, the properly placed rack 13 is placed between the projections 203 of the belt 201. In this way, since the rack 13 is conveyed while being sandwiched between the front-side guide 51 and back-side guide 52 and being placed between the projections 203, the projecting portion 134 of the rack 13 is removed from the slit 52s at a very low possibility. Therefore, the presence/absence of the rack 13 can be accurately detected by the normal placement detection unit at each placement position Pp during the convey operation. Since the presence/absence of the rack 13 is detected during the convey operation, whether or not the rack 13 is properly conveyed can be mechanically judged.

Conventionally, the rack may fall since it may tilt or vibrate vertically during the convey operation. The slit 52s has a role of mechanically limiting such position variations of the rack 13 in the vertical direction at the time of conveyance.

Figure 19:
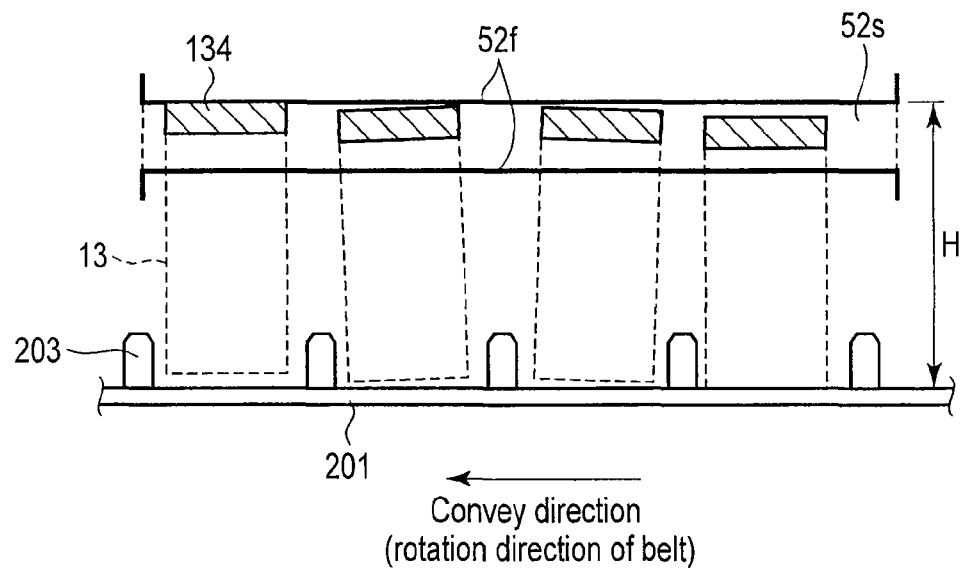
FIG. 19 is a view for explaining a falling prevention function of the rack at the time of conveyance using a groove shown in FIG. 18.

FIG. 19 is a view for explaining the falling prevention function of the rack 13 by the slit 52s at the time of conveyance. As shown in FIG. 19, the projecting portion 134 of the rack 13 is inserted into the slit 52s. The back-side guide 52 has edges 52f formed by the slit 52s. When the rack 13 tilts in the convey direction or jumps upward by vibrations, the upper end of the projecting portion 134 of the rack 13 collides against the edges 52f. In this manner, the upper edge 52f functions as a limiting portion which structurally limits position variations of the rack 13 in the vertical direction at the time of conveyance. In other words, the upper edge 52f functions as a guide of the rack 13 in the vertical direction. A lower limit of a height H of the upper edge 52f is set to be a height which allows insertion of the projecting portion 134 of the rack 13 at the time of placement. The lower limit of the height H of the upper edge 52f is limited to be equal to or smaller than a height corresponding to a maximum tilt angle at which the rack 13 can be restored by the self weight. That is, the height H of the upper edge 52f is set according to the length D2 of the projecting portion 134 in the thickness direction since the rack 13 can be restored by the self weight even when it tilts. By setting the height H of the edge 52f, the tilt angle of the rack 13 can be restored to 0° by the self weight of the rack 13 during the stop period in the convey operation.

As described above, the projecting portion 134 of the rack 13 is conveyed while being inserted into the slit 52s due to the structural limitations. Therefore, position variations of the rack 13 due to a tilt and vibrations can always be limited by the edge 52f at the time of conveyance. The rack 13 can only store a small number of cuvettes 11, has a relatively small bottom area, and relatively readily falls. However, according to this embodiment, position variations of the rack 13 at the time of conveyance can be minimized by the projections 203 of the belt 201, the front-side guide 51, the back-side guide 52, and the slit 52s. Therefore, the rack sampler 10 according to this embodiment can safely convey the rack 13.

(Effect)

As described above, the automatic analyzer 1 according to this embodiment can safely convey the rack 13 after the rack 13 is placed at an accurate position on the convey mechanism 20.

(First Modification)

In this embodiment, the convey mechanism controller 28 controls to execute and stop the convey operation using only a signal from the error placement detection unit 24 or signals from the error placement detection unit 24 and normal placement detection unit 26. However, this embodiment is not limited to this. For example, the convey mechanism controller 28 may control to execute and stop the convey operation using only a signal from the normal placement detection unit 26. More specifically, when a normal placement signal is output from the normal placement detection unit 26, the convey mechanism controller 28 according to a modification controls the convey mechanism driving unit 22 to continue the convey operation by the convey mechanism 20. When a normal placement signal is not output from the normal placement detection unit 26, the convey mechanism controller 28 controls the convey mechanism driving unit 22 to stop the convey operation. Therefore, when the rack 13 is not placed at a position which is proper for conveyance, the convey operation can be stopped. When the rack 13 is placed at a position which is proper for conveyance, the convey operation can be executed.

As described above, the automatic analyzer 1 according to the first modification can safely convey the rack 13 after the rack 13 is placed at an accurate position on the convey mechanism 20.

(Second Modification)

The automatic analyzer 1 according to this embodiment structurally limits position variations of the rack 13 along the vertical direction at the time of conveyance using the groove 52s formed in the back-side guide 52. However, this limitation method is applicable to only the rack 13 having the projecting portion 134. The automatic analyzer according to the second modification can also structurally limit position variations of the rack 13 having no projecting portion 134 along the vertical direction at the time of conveyance. In the following description, the same reference numerals denote components having roughly the same functions as those of this embodiment, and a repetitive description will be given only if it is necessary.

Figure 20:
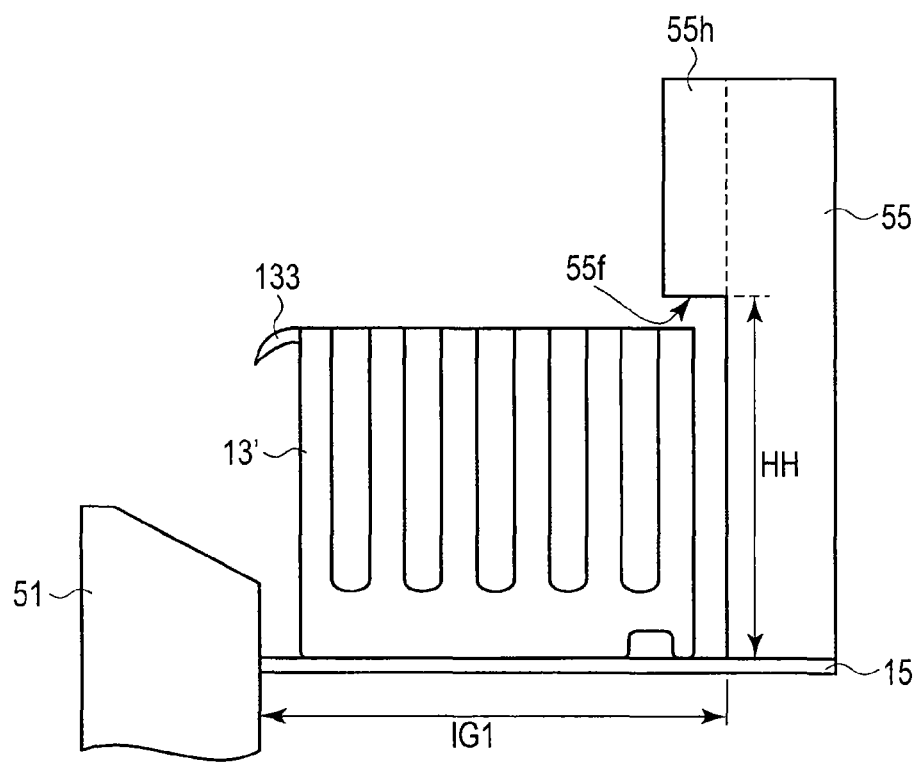
FIG. 20 is a view for explaining limitations on position variations in the vertical direction of the rack according to the second modification.

FIG. 20 is a view for explaining limitations of position variations in the vertical direction of a rack 13' according to the second modification. As shown in FIG. 20, the rack 13' according to the second modification does not have any projecting portion. A back-side guide 55 according to the modification is not formed with any slit. An overhang portion 55h which overhangs to the front side is formed on an upper portion of the back-side guide 55. The overhang portion 55h extends along the convey direction. When the rack 13' is properly placed, it is placed between the front-side guide 51 and a lower portion (without any overhang portion 55h) of the back-side guide 55, and an end portion of the rack 13' in the container layout direction (an end portion in a direction opposite to the grip portion 133) is placed under the overhang portion 55h. Therefore, an edge 55f on the bottom surface side of the overhang portion 55h functions as a limiting portion which structurally limits position variations of the rack 13' in the vertical direction at the time of conveyance. More specifically, when the rack 13' tilts in the convey direction or jumps upward due to variations, the upper end of the rack 13' collides against the edge 55f.

More specifically, a height HH of the edge 55f is set to be a height which allows insertion of the rack 13'. That is, a lower limit of the height HH is set to be slightly larger than the length D3 of the rack 13' in the height direction. An upper limit of the height HH is set to be a height corresponding to a maximum tilt angle at which the rack 13' can be restored by the self weight. That is, the height HH is set according to the length D2 in the thickness direction so that the rack 13' can be restored by the self weight even when it tilts. By setting the height HH of the edge 55f in this way, the tilt angle of the rack 13' can be restored to 0° by the self weight of the rack 13' during the stop period of the convey operation.

As described above, when the rack 13' is properly placed, it is placed between the front-side guide 51 and the lower portion (the portion without any overhang portion 55h) of the back-side guide 55, and is conveyed while the end portion of the rack 13' in the container layout direction (the end portion in the direction opposite to the grip portion 133) is kept placed under the overhang portion 55h. Therefore, position variations in the vertical direction due to a tilt and vibrations of the rack 13' can always be limited by the edge 55f at the time of conveyance. The rack 13' can only store a small number of cuvettes 11, has a relatively small bottom area, and relatively readily falls. However, according to this embodiment, position variations of the rack 13' at the time of conveyance can be minimized by the projections 203 of the belt 201, the front-side guide 51, the back-side guide 55, and the overhang portion 55h.

As described above, the automatic analyzer according to the second modification can safely convey the rack 13'.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

The invention claimed is:

1. An automatic analyzer comprising:
a convey mechanism configured to move a rack, which is configured to store a cuvette, along a predetermined linear moving direction;
a driving unit configured to drive the convey mechanism to intermittently move the rack along the moving direction;
an error placement detection unit configured to output an error placement signal when the error placement detection unit detects that a placement state of the rack on the convey mechanism corresponds to an error placement which does not allow the convey mechanism to normally convey the rack, and not to output the error placement signal when the error placement detection unit detects that the placement state does not correspond to the error placement; and
a controller configured to control the driving unit to stop a convey operation of the rack by the convey mechanism when the error placement signal is output and to execute the convey operation of the rack by the convey mechanism when the error placement signal is not output, wherein
the error placement detection unit detects entry of an improperly placed rack into a predetermined space region.

2. The automatic analyzer of claim 1, further comprising a warning unit configured to generate a warning when the error placement signal is output.

3. The automatic analyzer of claim 1, wherein the error placement detection unit includes a light source configured to emit light, and a detector configured to detect the light from the light source, and
the light source and the detector are disposed to sandwich a space region where at least a portion of the rack enters only when the rack is erroneously placed.

4. The automatic analyzer of claim 3, further comprising a guide which extends in the moving direction so as to guide movement of the rack in the moving direction,
wherein the light source and the detector are installed on the guide.

5. The automatic analyzer of claim 4, wherein the guide includes a slope portion configured to allow the rack to be slidable toward the convey mechanism by a weight of the rack when at least a portion of the rack rides on the guide, and
a wall portion which is formed below the slope portion and is configured to guide movement of the rack in the moving direction.

6. The automatic analyzer of claim 1, further comprising a normal placement detection unit configured to output a normal placement signal when the normal placement detection unit detects that the placement state corresponds to a normal placement which allows the convey mechanism to normally move, and not to output the normal placement signal when the normal placement detection unit detects that the placement state does not correspond to the normal placement,
wherein when the normal placement signal is output and when the error placement signal is not output, the controller controls the driving unit to execute the convey operation by the convey mechanism, and when the normal placement signal is output and the error placement signal is output, and when the normal placement signal is not output, the controller controls the driving unit to stop the convey operation by the convey mechanism, and
the normal placement detection unit detects entry of a properly placed rack into a predetermined space region.

7. The automatic analyzer of claim 6, further comprising a warning unit configured to generate a warning when the normal placement signal is output and the error placement signal is output, and when the normal placement signal is not output.

8. The automatic analyzer of claim 6, wherein the normal placement detection unit includes a light source configured to emit light and a detector configured to detect the light from the light source, and
the light source and the detector are disposed to sandwich a space region where at least a portion of the rack enters only when the rack is normally placed.

9. An automatic analyzer comprising:
a convey mechanism configured to move a rack, which is configured to store a cuvette, along a predetermined linear moving direction;
a driving unit configured to drive the convey mechanism to intermittently move the rack along the moving direction;
a normal placement detection unit configured to output a normal placement signal when the normal placement detection unit detects that a placement state of the rack on the convey mechanism corresponds to a normal placement which allows the convey mechanism to normally convey the rack, and not to output the normal placement signal when the normal placement detection unit detects that the placement state does not correspond to the normal placement; and
a controller configured to control the driving unit to continue a convey operation by the convey mechanism when the normal placement signal is output, and to stop the convey operation by the convey mechanism when the normal placement signal is not output, wherein
the normal placement detection unit detects entry of a properly placed rack into a predetermined space region.

10. The automatic analyzer of claim 9, further comprising a warning unit configured to generate a warning when the normal placement signal is not output.

11. The automatic analyzer of claim 9, wherein the normal placement detection unit includes a light source configured to emit light and a detector configured to detect the light from the light source, and
the light source and the detector are disposed to sandwich a space region where at least a portion of the rack enters only when the rack is normally placed.

12. The automatic analyzer of claim 11, further comprising a guide which extends in the moving direction to guide movement of the rack in the moving direction,
wherein the light source and the detector are installed on the guide.

13. The automatic analyzer of claim 12, wherein the guide has a slit which extends parallelly along the moving direction and allows insertion of a projecting portion of the rack,
the light source and the detector are arranged on the guide to face each other and to sandwich the slit, and
the slit is formed in the guide to allow insertion of the projection portion only when the rack is normally placed.

* * * * *